(12) United States Patent
Arepally et al.

(10) Patent No.: US 12,390,621 B1
(45) Date of Patent: *Aug. 19, 2025

(54) SYSTEM AND METHOD FOR SELECTIVE PRESSURE-CONTROLLED THERAPEUTIC DELIVERY

(71) Applicant: TriSalus Life Sciences, Inc., Westminster, CO (US)

(72) Inventors: Aravind Arepally, Atlanta, GA (US); James E. Chomas, Denver, CO (US); Bryan Pinchuk, Miami, FL (US); David Benjamin Jaroch, Arvada, CO (US)

(73) Assignee: TriSalus Life Sciences, Inc., Westminster, CO (US)

( * ) Notice: Subject to any disclaimer, the term of this patent is extended or adjusted under 35 U.S.C. 154(b) by 62 days.

This patent is subject to a terminal disclaimer.

(21) Appl. No.: 17/671,296

(22) Filed: Feb. 14, 2022

Related U.S. Application Data

(63) Continuation of application No. 15/871,326, filed on Jan. 15, 2018, now Pat. No. 11,400,263, which is a
(Continued)

(51) Int. Cl.
*A61M 25/10* (2013.01)
*A61F 2/01* (2006.01)
(Continued)

(52) U.S. Cl.
CPC ............. *A61M 25/10* (2013.01); *A61F 2/013* (2013.01); *A61L 29/16* (2013.01); *B05D 1/18* (2013.01);
(Continued)

(58) Field of Classification Search
CPC .. A61M 25/10; A61M 25/0108; A61M 39/22; A61M 2230/30; A61M 2230/06; A61M 2039/229; A61M 2025/1052
(Continued)

(56) References Cited

U.S. PATENT DOCUMENTS

| 4,738,740 A | 4/1988 | Pinchuk et al. |
| 5,171,299 A | 12/1992 | Heitzmann |

(Continued)

FOREIGN PATENT DOCUMENTS

| EP | 1743524 A1 * | 1/2007 | ........... A01K 67/027 |
| JP | 2002537909 | 11/2002 | |

(Continued)

OTHER PUBLICATIONS

Canadian Office Action 2 dated Jun. 3, 2022 of Application No. 3,139,118.
(Continued)

*Primary Examiner* — Phillip A Gray
(74) *Attorney, Agent, or Firm* — Wan Chieh Lee; Trenton D. Hatherill; Haug Partners LLP

(57) ABSTRACT

A treatment system includes a guide sheath, and a catheter provided with a pressure-controlled element. The pressure-control element preferably includes an expanded configuration adapted to extend across a small feeder vessel branching from the splenic vein. The pressure-control element is positioned with the feeder vessel, and a therapeutic agent is delivered under pressure directly into the feeder vessel, where it is forced to penetrate deep into tissue. Pressure responsive elements for monitoring intravascular pressure are also provided to time delivery of the therapeutic agent for maximum uptake by the target organ. Methods for treating tissues and organs via vascular pathways are provided.

25 Claims, 17 Drawing Sheets

Related U.S. Application Data continuation-in-part of application No. 15/703,951, filed on Sep. 13, 2017, now Pat. No. 10,780,250.

(60) Provisional application No. 62/396,622, filed on Sep. 19, 2016.

(51) Int. Cl.

| | |
|---|---|
| *A61L 29/16* | (2006.01) |
| *A61M 39/22* | (2006.01) |
| *B05D 1/18* | (2006.01) |
| *B05D 3/02* | (2006.01) |
| *A61M 25/01* | (2006.01) |

(52) U.S. Cl.
CPC ...... *B05D 3/0272* (2013.01); *A61F 2240/001* (2013.01); *A61L 2430/36* (2013.01); *A61M 25/0108* (2013.01); *A61M 2025/1052* (2013.01); *A61M 39/22* (2013.01); *A61M 2039/229* (2013.01); *A61M 2205/3334* (2013.01); *A61M 2230/06* (2013.01); *A61M 2230/30* (2013.01)

(58) Field of Classification Search
USPC ........................................................ 604/500
See application file for complete search history.

(56) References Cited

U.S. PATENT DOCUMENTS

| | | | | |
|---|---|---|---|---|
| 5,397,308 | A | 3/1995 | Ellis | |
| 5,534,287 | A | 7/1996 | Lukic | |
| 6,641,553 | B1* | 11/2003 | Chee | A61B 17/32037 604/68 |
| 6,699,231 | B1 | 3/2004 | Sterman et al. | |
| 6,743,196 | B2 | 6/2004 | Barbut | |
| 8,696,698 | B2 | 4/2014 | Chomas et al. | |
| 9,737,693 | B2 | 8/2017 | Helkowski | |
| 11,090,468 | B2 | 8/2021 | Chappa | |
| 11,324,619 | B1 | 5/2022 | Yacoby | |
| 11,400,263 | B1* | 8/2022 | Arepally | A61M 25/10 |
| 2001/0041862 | A1* | 11/2001 | Glickman | A61M 1/3615 604/101.03 |
| 2003/0135255 | A1 | 7/2003 | Sundar | |
| 2004/0006305 | A1 | 1/2004 | Hebert | |
| 2004/0063805 | A1 | 4/2004 | Pacetti et al. | |
| 2004/0098099 | A1 | 5/2004 | McCullagh et al. | |
| 2004/0167385 | A1 | 8/2004 | Rioux et al. | |
| 2005/0113798 | A1 | 5/2005 | Slater | |
| 2006/0149141 | A1 | 7/2006 | Sheets | |
| 2006/0178695 | A1 | 8/2006 | DeCant et al. | |
| 2006/0263301 | A1 | 11/2006 | Vernon | |
| 2006/0264898 | A1* | 11/2006 | Beasley | A61B 6/12 428/36.9 |
| 2007/0042018 | A1 | 2/2007 | Shalaby | |
| 2007/0191931 | A1 | 8/2007 | Weber et al. | |
| 2008/0051758 | A1 | 2/2008 | Rioux | |
| 2008/0234796 | A1 | 9/2008 | Dorn | |
| 2009/0060973 | A1 | 3/2009 | Hunter et al. | |
| 2010/0069841 | A1 | 3/2010 | Miesel | |
| 2010/0113939 | A1 | 5/2010 | Mashimo et al. | |
| 2014/0276411 | A1* | 9/2014 | Cowan | A61B 6/481 604/143 |
| 2014/0364835 | A1 | 12/2014 | Allen et al. | |
| 2015/0272716 | A1 | 10/2015 | Pinchuk et al. | |
| 2015/0306311 | A1 | 10/2015 | Pinchuk et al. | |
| 2016/0082178 | A1 | 3/2016 | Agah et al. | |
| 2016/0242893 | A1 | 8/2016 | Joshi et al. | |
| 2016/0249969 | A1 | 9/2016 | Santoinanni | |
| 2016/0310148 | A1* | 10/2016 | Allen | A61B 17/12136 |
| 2017/0368306 | A1* | 12/2017 | Tal | A61M 25/0074 |
| 2020/0205840 | A1 | 7/2020 | Adawi | |
| 2020/0383688 | A1 | 12/2020 | Olson | |
| 2021/0244473 | A1 | 8/2021 | Cook | |
| 2023/0025500 | A1 | 1/2023 | Jaroch et al. | |

FOREIGN PATENT DOCUMENTS

| | | |
|---|---|---|
| JP | 2006051144 A | 2/2006 |
| JP | 2006523515 | 10/2006 |
| WO | 9902093 A1 | 1/1999 |
| WO | WO 2000051675 | 9/2000 |
| WO | 02055146 A1 | 7/2002 |
| WO | 2004075776 | 9/2004 |
| WO | WO 2011068946 | 6/2011 |
| WO | 2016149653 | 9/2016 |
| WO | WO 2018175148 | 9/2018 |
| WO | WO 2019140381 | 7/2019 |

OTHER PUBLICATIONS

International Search Report and Written Opinion of Application No. PCT/US2020/034626 dated Aug. 26, 2020.

Japanese Office Action dated Apr. 28, 2021 of Application No. 2020-082002.

Japanese Office Action dated May 10, 2022 of Application No. 2021-572025.

U.S. Appl. No. 17/375,779, Arepally et al.

U.S. Appl. No. 19/054,055, Arepally et al.

Jedwab et al., A Study of the Geometrical and Mechanical Properties of a Self-Expanding Metallic Stent Theory and Experiment, Journal of Applied Biomaterials, Spring 1993, pp. 77-85, 4.1.

Rose et al., Temporary Splenic Artery Balloon Occlusion for Protection of Nonsplenic Vascular Beds During Splenic Embolization, American Journal of Roentgenology, May 1998, pp. 1186-1188, 170.5.

Rose et al., Downstream Hepatic Arterial Blood Pressure Changes Caused by Deployment of the Surefire AntiReflux Expandable Tip, Cardiovascular and Interventional Radiology, Oct. 2013, pp. 1262-1269, 36.

Rose et al., Feasibility of Intraprocedural Transluminal Hepatic and Femoral Artery Blood Pressure Measurements as an Alternative Embolization Safety Endpoint When Antireflux Devices Are Used During Lobar Chemoembolization, American Journal of Roentgenology, Jul. 2015, pp. 196-202, 205.1.

Rose et al., Quantification of Blood Pressure Changes in the Vascular Compartment When Using an Anti-Reflux Catheter during Chemoembolization versus Radioembolization: A Retrospective Case Series, Journal of Vascular and Interventional Radiology, Jan. 2017, pp. 103-110, 28.1.

Rose et al., The Beauty and Bane of Pressure-Directed Embolotherapy: Hemodynamic Principles and Preliminary Clinical Evidence, American Journal of Roentgenology, Mar. 2019, pp. 686-695, 212.3.

Iranpour et al. Altered Doppler Flow Patterns in Cirrhosis Patients: An Overview, Ultrasonography, Jan. 2016, pp. 2-12, 35.1.

* cited by examiner

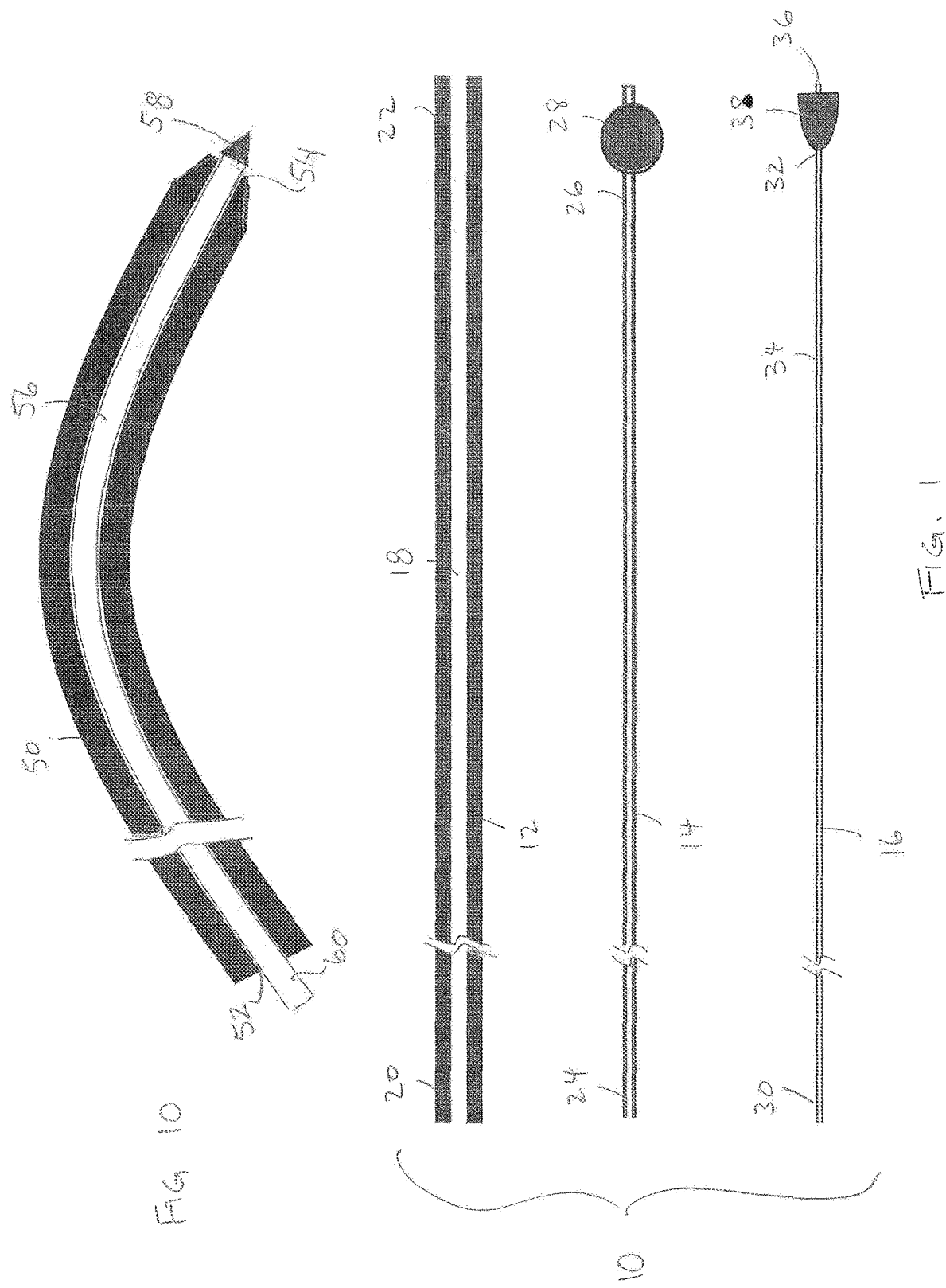

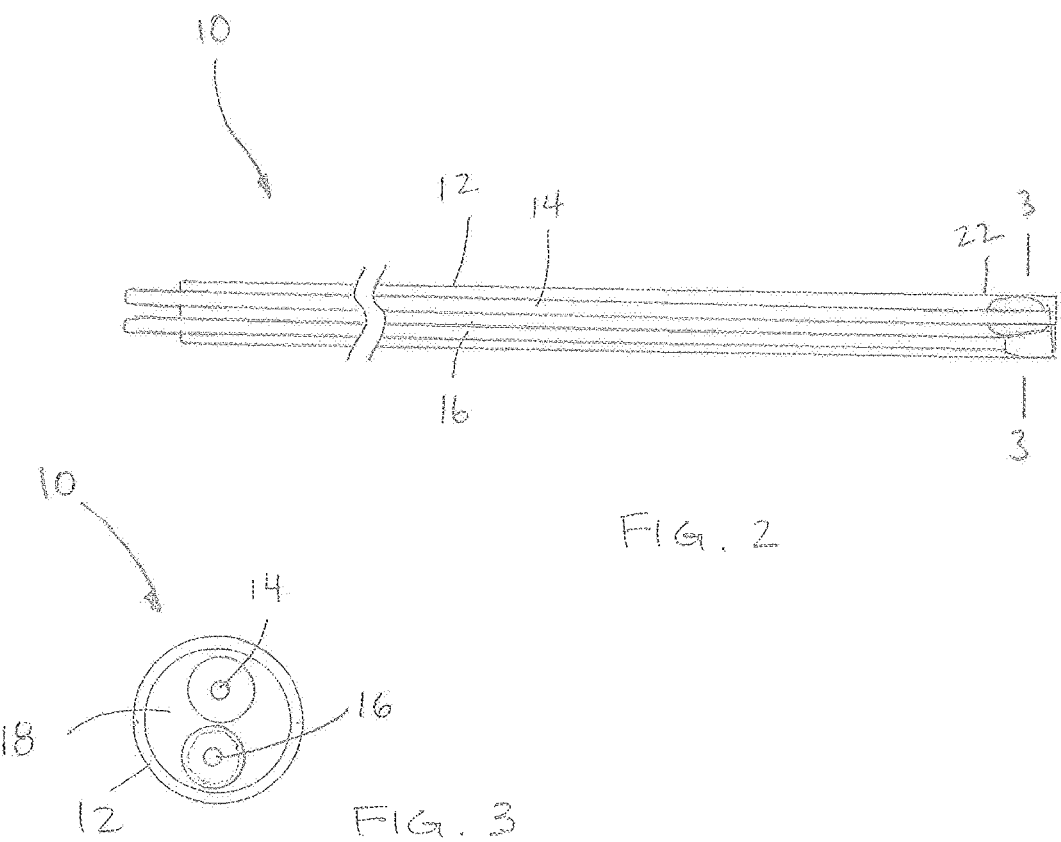

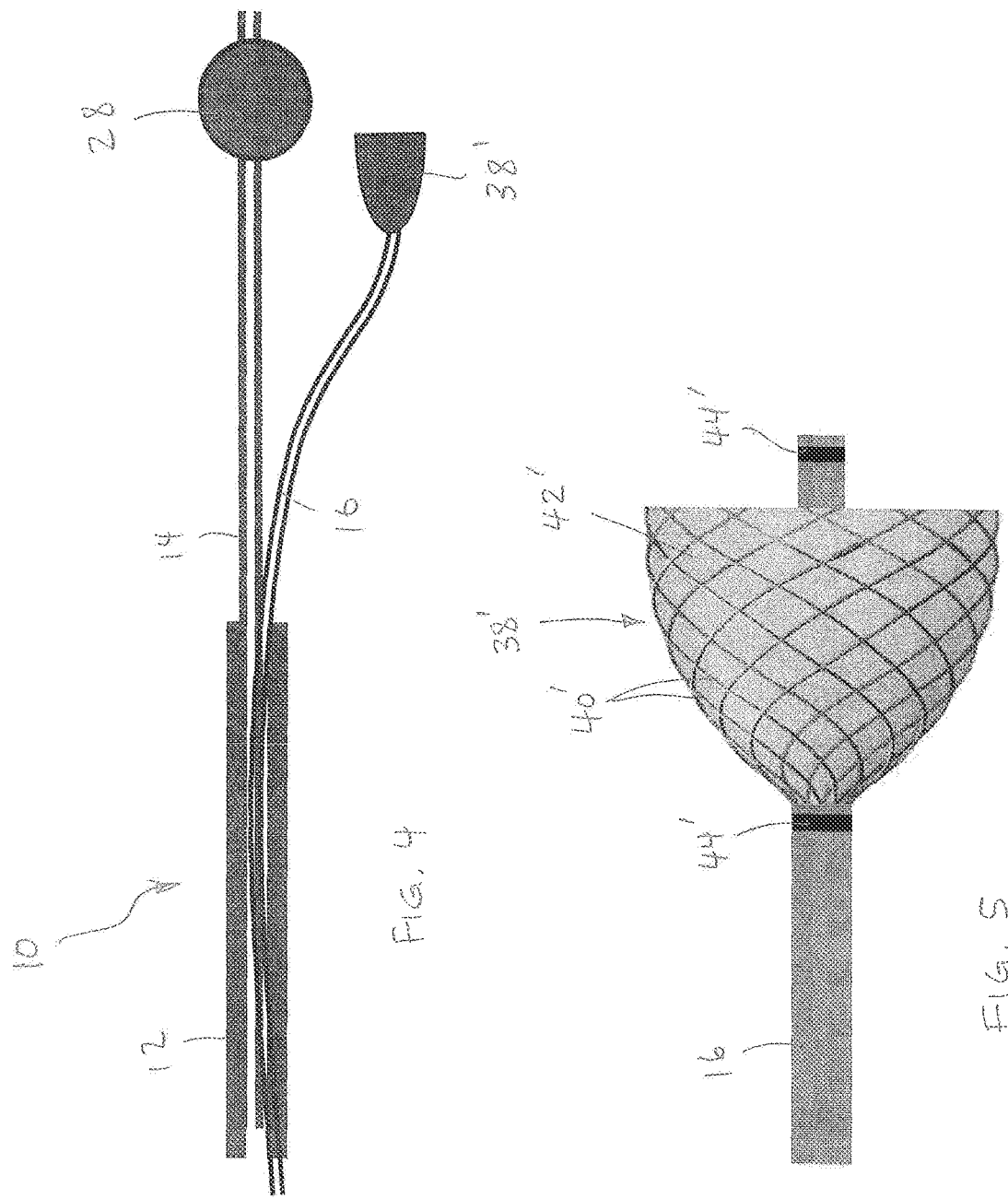

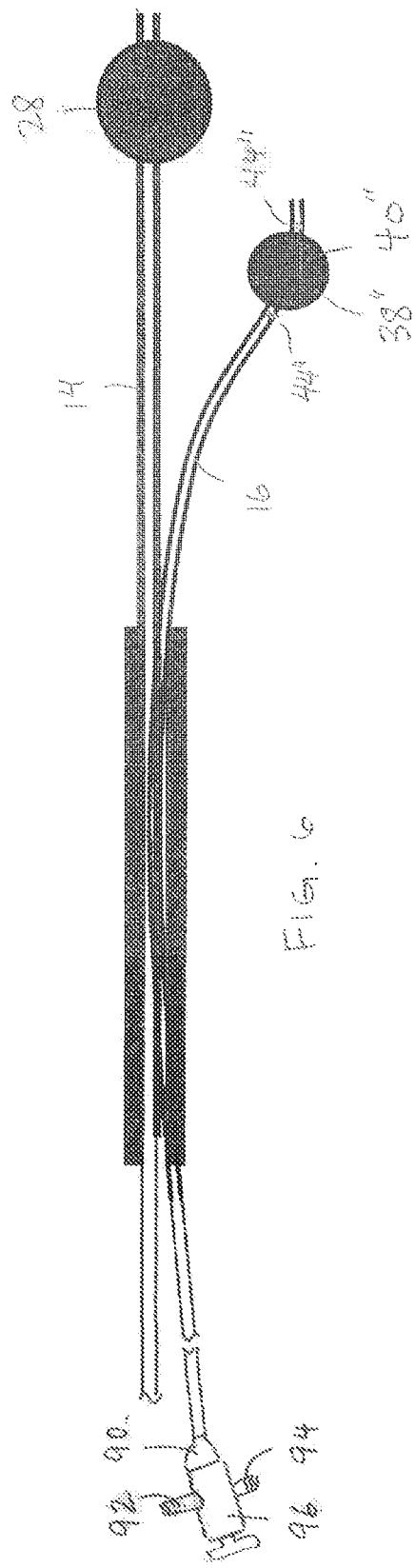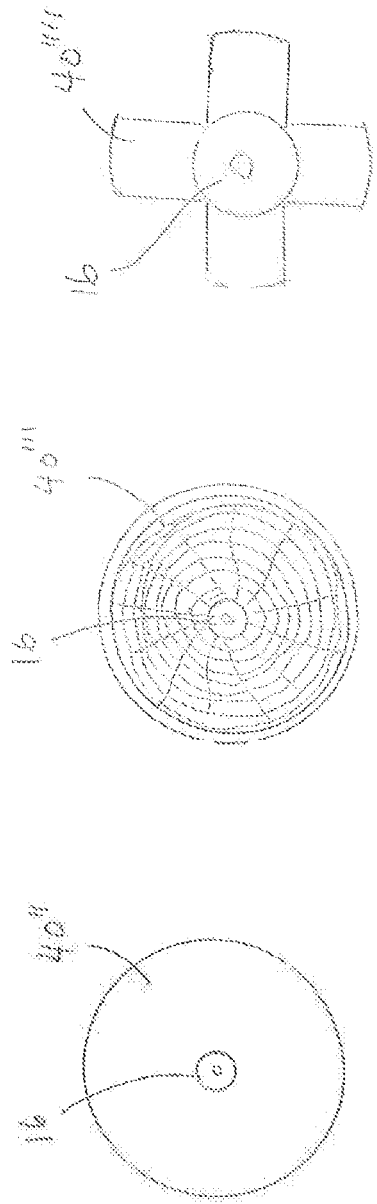

SYSTEM AND METHOD FOR SELECTIVE PRESSURE-CONTROLLED THERAPEUTIC DELIVERY

CROSS-REFERENCE TO RELATED APPLICATIONS

This application is a continuation of U.S. Ser. No. 15/871,326, filed Jan. 15, 2018, which is a continuation-in-part of U.S. Ser. No. 15/703,951, filed Sep. 13, 2017, now U.S. Pat. No. 10,780,250, which claims benefit to U.S. Provisional Application Ser. No. 62/396,622, filed Sep. 19, 2016, which are hereby incorporated by reference herein in their entireties.

BACKGROUND OF THE INVENTION

1. Field of the Invention

The medical devices and method described herein relate generally to medical devices and methods for infusing a treatment through a vessel to a target tissue for the treatment of cancer or other diseases.

2. State of the Art

In some instances, systemic treatments are used to treat disease within a patient. The effectiveness of some such systemic treatments can vary due at least in part to the treatment (e.g., a radio-embolization agent, a biologic agent and/or other treatment formulation) not reaching target tissue. For example, in the treatment of some diseases such as pancreatic cancer and/or diabetes, it may be desirable to deliver biological cells to the pancreas where efficient and safe engraftment can be achieved, especially to the pancreatic tail, for example, where a large number of the endogenous islet cells reside. Specifically, in some instances, some systemic treatments of diabetes, which affects the body's ability to produce and/or regulate insulin, have attempted to transplant insulin producing beta cells into pancreatic tissue, however, with limited success due to a lack of supply and a long term need for immunosuppression. In other forms of treatment for diabetes, transplantation of autologous stem cells (mesenchymal, bone marrow, and others) can increase and/or replace the supply of insulin, especially in Type II diabetes where autoimmune reaction against these cells appears limited. In such treatments, various methods have been used such as, for example, transplanting the cells surgically in the sub capsular space in the kidney, the liver, and nonselective systemic injection both intravenously and intra-arterially, with the hope of "homing" these cells to the pancreatic tissue to allow engraftment, however, a best mode of transplantation has yet to established.

In some instances, a treatment can include transplanting such cells into the pancreas itself. For example, one treatment has included sub-selective endovascular injection of these cells into the arterial supply of the pancreatic tissue. Such an approach, however, is subject to variation in the number of cells actually introduced to the pancreas (versus other organs in the same vascular bed including the spleen, the liver, and/or the stomach). Furthermore, inadvertent exposure of other non-target organs to such cells can result in health risks for the patient.

Treatments for pancreatic cancer can be similarly ineffective. For example, pancreatic cancer is considered an almost chemoresistant tumor. The ineffective result of systemic chemotherapy is at least in part due to an insufficient drug concentration within the tumor because of dose-limited toxicity in bone marrow and epithelial tissue. Since systemic chemotherapy is limited in its effectiveness, treatments beyond systemic chemotherapy can be desirable for advanced pancreatic cancer patients. For example, one such treatment can include local intra-arterial delivery of chemotherapy. Intra-arterial infusion allows higher drug concentration to reach the tumor. Furthermore, intra-arterial chemotherapy can also take advantage of the first pass effect of chemotherapeutics, generating higher-level drug concentrations at the tumor cell membrane and therefore, enhancing cellular drug uptake as compared to intravenous infusion. Lastly, local delivery can reduce systemic side effects.

Intra-arterial chemotherapy treatment is usually administered through small catheters placed in the celiac/hepatic artery or portal vein. An issue in catheter localization is the redundant nature of blood supply to the pancreas overlapping adjacent organs. Furthermore, the small size and anatomical variability of the branches of the hepatic and splenic arteries to the pancreas precludes reproducible cannulization via interventional techniques. Delivering the therapy to the correct location requires knowledge of the patient's arterial anatomy, preferably obtained through visualization techniques in advance of therapeutic delivery of the treatment.

Even then, standard catheters permit limited control of the infused treatment. The treatment will flow from an area of high pressure to an area of lower pressure. Given the cyclic pressure operating on the blood as the heart beats, the treatment can reflux into healthy tissues where it will do harm, rather than good.

In order to alleviate certain of these issues, co-owned U.S. Pat. No. 8,696,698 to Chomas describes a pressure-controlled therapeutic delivery device in the form of a microvalve mounted at the distal end of catheter. The microvalve dynamically expands and contracts within a blood vessel in relation to the surrounding blood pressure. A treatment can be infused through the catheter under significant pressure. When the treatment agent is infused, the pressure in the vessel downstream (distal) of the treatment is always higher than that upstream (proximal) of the treatment, causing the microvalve to open and block reflux of the agent.

One issue to using the Chomas pressure-controlled therapeutic delivery device for delivery of a therapeutic agent to the pancreas is that the portal vein, which extends through the pancreas, is open to the spleen. The spleen has the capacity to store a large volume of blood. As such, any therapeutic agent injected into the portal vein will travel to the spleen rather than into the smaller feeder vessels off of the portal vein. Therefore, the therapeutic agent may not reach desirable therapeutic concentrations deep within the pancreas, where needed.

US Pub. No. 2016/0082178 to Agah discloses a device and method for isolating and visualizing feeder vessels using an endovascular approach. The device includes an outer catheter and an inner catheter longitudinally displaceable in a telescoping arrangement. An occlusive element is coupled to each catheter. The outer catheter includes side openings, and an agent can be infused through the outer catheter and out of the side openings between the two occlusive elements. In use, the device is advanced to the portal vein, and the catheters are displaced to locate the occluders on opposing sides of feeder vessels. The occluders are then expanded to isolate a region of the portal vein containing the feeder vessels, thereby causing cessation of blood flow within the isolated region. Then a contrast agent is injected through the outer catheter, out the side openings, and into the portal vein, where it travels only within the isolated region of the portal vein and off to the feeder vessels of the portal vein to visualize the vessels. A similar subsequent step can be performed to inject a therapeutic agent into the portal vein and feeder vessels.

This system has several disadvantages. As the portal vein does not have significant tubular strength and can expand when subject to the increased pressure of the injected therapeutic agent, the agent may flow around the occluders and out into areas that are not intended to receive the agent. This would result in a reduced concentration of therapeutic agent in the feeder vessels where it is most needed and may also result in therapeutic agent travelling to and detrimentally acting upon unintended tissues. In addition, if the occluders are expanded to too large a size to attempt to prevent leakage, the vessels can be damaged. Further, the release of the therapeutic agent is into the portal vein; however, the size of the opening or openings in the catheter for release of the therapeutic agent is very small in relation to the diameter of the portal vein, further preventing generation of the pressure desired to saturate and penetrate the intended tissues with the therapeutic agent.

SUMMARY OF THE INVENTION

A system is provided for the treatment of an organ with a vascular-infused therapeutic agent. In an embodiment, the system includes an outer guide sheath having proximal and distal ends, a first catheter longitudinally displaceable within the outer guide sheath and provided with one distal occlusion device, and a second catheter longitudinally displaceable within the outer guide sheath and provided with another distal occlusion device.

In an embodiment, the first and second catheters are arranged parallel and non-coaxial within the guide sheath.

In another embodiment, the first and second catheters are coaxial.

In another embodiment, the second catheter extends parallel and coaxially within a portion of the first catheter, but the first catheter is adapted permit the second catheter to extend outside the first catheter at a location proximal of the first distal occlusion device so that the distal occlusion devices are non-coaxial in a treatment configuration.

In an embodiment, one distal occlusion device has an expanded configuration sized to extend across a small feeder vessel branching from a larger blood vessel, and the first catheter is adapted to deliver therapeutic agent out of an orifice located at the distal end of the first catheter to exit on a distal side of the occlusion device.

In an embodiment, the system is limited to the first occlusion device, alone, without any other occlusion device.

In an embodiment, first and second distal occlusion devices are provided, and the first occlusion device is preferably a static device, e.g., a balloon, and the second occlusion device is dynamic. The first occlusion device preferably, at least in use and optionally in design and structure, expands to a larger maximum diameter than the second occlusion device, as it is intended for use in, and to extend across and block fluid flow within, a larger vessel (e.g., the splenic vein) than the second occlusion device is intended (e.g., the feeder vessels).

The second occlusion device is configured to permit injection of an infusate under relatively high pressure; i.e., a pressure-control element. The pressure-control element may be a dynamic device or a static device.

A dynamic pressure-control element may include a microvalve that automatically expands to the diameter of the vessel in which it is deployed when subject to predetermined fluid pressure conditions and contracts to a smaller diameter when subject to relatively lower fluid pressure conditions. A microvalve suitable for use preferably includes a microporous polymer advantageously formed by electrospinning or dip-coating a polymer over a filamentary braid having a frustoconical portion. The microporous polymer allows generation of fluid pressure at one side of the microvalve, while blocking particles on the pressurized side of the microvalve that exceed 5 µm from passing through the microvalve.

A static pressure-control element includes a fluid inflatable balloon, a self-expanding filter, and a mechanically expandable malecot catheter. These elements cause occlusion of the vessel by being sufficiently expanded to block flow within a vessel around the static pressure-controlled element, and do not modulate in expansion in view of localized fluid pressure conditions within the vessel.

In an embodiment, an implantable injection port is provided at the proximal end of the first and second catheters, and a distal occlusion device is provided at the distal ends of the first and second catheters. The injection port includes a first chamber into which a therapeutic agent can be injected and which is in fluid communication with the distal orifice. In an embodiment, the injection port can be operable to cause longitudinal displacement of the first and second catheter to cause movement of the distal occlusion device between collapsed and expanded diameters. Displacement of the catheters may be effected application of mechanical, electrical or magnetic energy to the injection port. In another embodiment, the injection port includes a second chamber which when expanded under pressure of a fluid causes the distal occlusion device to expand. The injection port is composed of a material that is biocompatible when implanted subdermally, and which minimizes thrombus formation and tissue encapsulation.

In an embodiment, the system also includes a pressure-detecting element and/or an infusion timing element adapted to permit injection of the infusate based on a localized pressure or timing event.

In an embodiment, such pressure-detecting element permits injection of the infusate during an intended blood pressure, change in blood pressure, or at a prescribed time delay relative to a change in pressure at the heart or in the target organ. The pressure-detecting element can, e.g., permit or activate infusion during the diastolic period and halt or deactivate infusion during the systolic period; this increases pressure differential and maximizes organ uptake of the infusate. By way of example, the pressure-detecting element may include a pressure sensor and optionally a pump.

In an embodiment, the infusion timing element is adapted to permit injection of the infusate at a set time offset following a portion of the cycle of the heart rate, with such delay capable of accounting for a consequent change in pressure occurring in the target organ after a pressure change at the heart. By way of example, the timing element may include a connection to an EKG or pulse-oximeter and optionally a pump.

The system may also include an access needle provided with a piercing tip and a distal opening. The access needle may be curved. The piercing tip may be in the form of a removable obturator, which when removed exposes the distal opening. The piercing tip is configured and sized to directly pierce the portal vein and enter into the interior of the portal vein in a manner that communicates the distal opening of the access needle with the interior of the portal vein. In an embodiment, the access needle includes a lumen sized to permit longitudinal passage of the guide sheath therethrough. The system may also include an exchange device to facilitate displacement of the access needle over the guide sheath, particularly after the guide sheath has been inserted into the portal vein.

In one embodiment of use, the access needle is deployed directly into the portal vein without traversing other endovascular vessels. This is achieved by directly puncturing the portal vein with the aid of ultrasound visualization. In an embodiment, a guide catheter is then advanced through the access needle and into the portal vein. In an embodiment, the first catheter is then advanced out of the guide catheter, through the portal vein and into the splenic vein traversing the pancreas and toward the spleen. A preferably static occlusion device is provided at the end of the first catheter and in the splenic vein adjacent the spleen. The occlusion device is expanded to occlude the splenic vein.

In an embodiment, a contrast agent is then infused through the guide catheter (either around the first and second catheters, or within a dedicated lumen) and out into the portal vein and to the splenic vein providing visualization of the splenic vein and feeder vessels extending off of the splenic vein and deep into the pancreas. In an embodiment, the first occlusion device may then remain in the expanded state; alternatively, it may be collapsed to again permit blood flow within the splenic vein up to the portal vein. A guidewire is then advanced through the second catheter and, under guidance of the imaging provided by the contrast agent, guided into a first feeder vessel extending from the splenic vein.

In an embodiment, the second catheter is then advanced over the guidewire so that another occlusion device at the end thereof is at or beyond the ostium of the first feeder vessel. If the occlusion device on the second catheter is a static device, it is then expanded to block passage within the first feeder vessel. If the occlusion device on the second catheter is dynamic, no pre-expansion is required, as the occlusion device will automatically expand when subject to the increased fluid pressure of the injected treatment agent.

The treatment agent is then injected under pressure through the second catheter and into the feeder vessel. When the pressure within the feeder vessel is higher than the systemic pressure and the occluder device on the second caterer is expanded open into atraumatic contact with the vessel wall, the treatment agent is prevented from flow outside the region of the feeder vessel and is forced deep into the pancreatic tissue. Moreover, the treatment agent is forced into hypoxic regions of tissue which are not serviced by circulating blood flow; thus the treatment remains in the tissue and can be effective for a relatively long period of time. Another way to increase the pressure is by providing the second catheter in a diameter that approaches the size the feeder vessel so that a large pressure head can be developed. Yet another way in which this may be accomplished is by adapting the second occlusion device so that it can automatically accommodate the size of the vessel wall, even if the vessel wall expands in diameter. These approaches can be used individually or in combination.

In an embodiment of use, the blood pressure or a change in blood pressure is detected and the treatment agent is injected through the second catheter only sensing that the pressure in the target organ or at the heart meets a sensed condition. Once the condition is met, the system may permit manual injection or may include a pump that automatically injects the treatment agent.

In another embodiment of use, combinable with the aforementioned method or used without, the treatment agent is injected after a prescribed time following a sensed condition. At the prescribed time following the sensed condition, the system may permit manual injection or may include a pump that automatically injects the treatment agent.

In an embodiment, the infusion timing element is adapted to permit injection of the infusate at a set time offset following a portion of the cycle of the heart rate, with such delay capable of accounting for a consequent change in pressure occurring in the target organ after a pressure change at the heart. By way of example, the timing element may include a connection to an EKG or pulse-oximeter and optionally a pump.

Embodiments are also provided for using the system to treat tumors in various organs throughout the human body.

BRIEF DESCRIPTION OF THE DRAWINGS

FIG. 1 is a schematic illustration of a kit that can be assembled into a treatment system for performing pressure-controlled therapeutic delivery.

FIG. 2 is a schematic illustration of an embodiment of the assembled system in which the first and second catheters extend within a guide catheter.

FIG. 3 is cross-section across line 3-3 in FIG. 2.

FIG. 4 is a schematic illustration of one embodiment of a distal end of treatment system for performing pressure-controlled therapeutic delivery.

FIG. 5 is a dynamic occlusion element of the treatment system shown in FIG. 4.

FIG. 6 is a schematic illustration of another embodiment of a treatment system for performing pressure-controlled therapeutic delivery.

FIG. 7 is a first static occlusion element for the treatment system shown in FIG. 6.

FIG. 8 is a first static occlusion element for the treatment system shown in FIG. 6.

FIG. 9 is a first static occlusion element for the treatment system shown in FIG. 6.

FIG. 10 is a schematic illustration of an access needle of a kit and system for performing pressure-controlled therapeutic delivery.

DETAILED DESCRIPTION OF THE PREFERRED EMBODIMENTS

Figure 11:
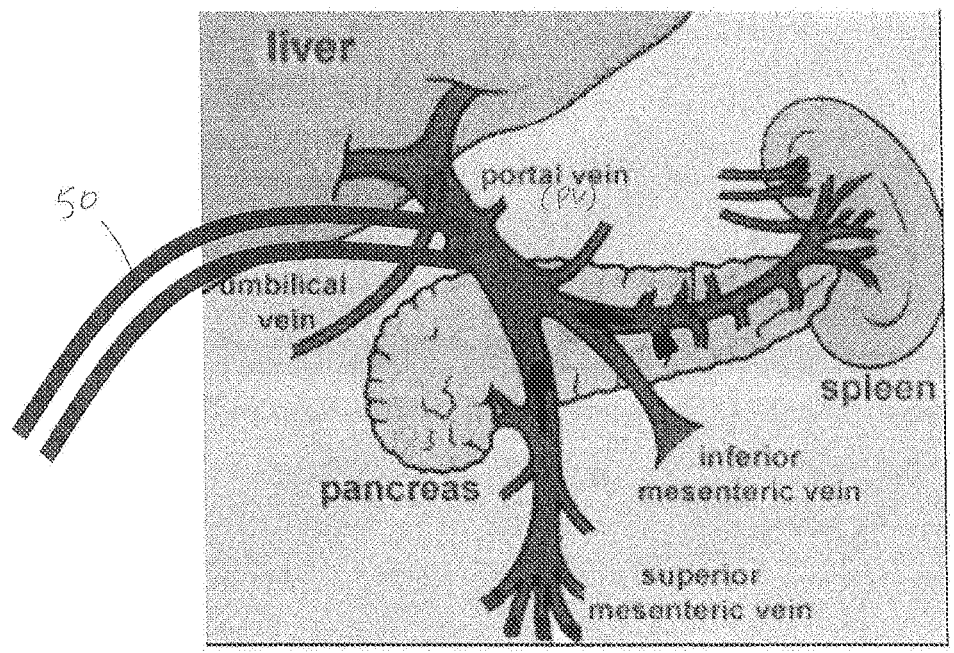
FIGS. 11 through 14 illustrate a method for performing pressure-controlled therapeutic delivery.

With reference to the following description, the terms "proximal" and "distal" are defined in reference to the hand of a user of the devices and systems described herein, with the term "proximal" being closer to the user's hand, and the term "distal" being further from the user's hand such as to often be located further within a body of the patient during use.

Apparatus and methods are described herein related to the use of a system to inject a contrast agent into a primary vessel and use the visualization provided by the contrast agent to identify feeder vessels leading from the primary vessel and communicating with, for example, a tumor or to identify one or more feeder vessels leading to a site of vasculature bleeding. For example, the tumor to be treated can be a solid tumor. In some cases, the tumor can be a cancerous tumor, such as a tumor specific to, for example, cancer of the pancreas, colon, liver, lung, or uterus. Various examples are provided below.

As described herein, a treatment system is used to provide a treatment agent around, for example, a solid tumor, to permit targeted treatment of a region by the treatment agent, isolation of the treatment agent within the target region, all without isolating a larger region than necessary from blood flow during the treatment procedure. In some cases, the solid tumor is associated with cancer of the pancreas, colon, liver, lung or uterus. With the treatment system in place, the treatment agent (e.g., an immunotherapy agent, chemoembolization agent, radio-embolization agent, in combination with a contrast dye) can be injected under pressure into a region of an organ or other defined area of tissue served by one or more feeder vessels. As such, the treatment system is used to identify small tumor feeder vessels connected to a tumor and selectively inject a treatment agent under pressure into the small tumor feeders.

In embodiments, the method includes introducing a treatment system into a target vessel within a patient where the target vessel is near a tumor. The target vessel may be an artery or vein. The target vessel may lead or extend within any of various organs, including, but not limited to, the pancreas, colon, liver, lung, uterus, prostate or brain, as well as target vessels communicating with head and neck tumors. In embodiments, the treatment system may be introduced into or adjacent the target vessel non-endovascularly. In embodiments, the treatment system may be introduced into the target vessel or into an adjacent vessel communicating with the target vessel directly through an access needle.

Referring now to FIGS. 1, 2 and 3, an embodiment of the treatment system 10 includes an outer guide sheath 12, and a first catheter 14 and a second catheter 16. The guide sheath 12 has proximal and distal ends 20, 22, and a lumen 18 extending between its ends. The first and second catheters 14, 16 are arranged parallel. In an embodiment, the first and second catheters 14, 16 extend non-coaxial within the lumen 18 of the guide sheath 12, and are longitudinally displaceable relative to guide sheath such that each can be extended out of the distal end 22, and retracted back into the lumen 18 of the guide sheath.

The first catheter 14 has proximal and distal ends 24, 26, and is provided with a first distal occlusion device 28 at its distal end 26. The second catheter 16 has proximal and distal ends 30, 32, and a lumen 34 extends therethrough. A distal pressure-control element 38 is mounted at the distal end 32, and a distal orifice 36 of the lumen opens distally of the pressure-control element 38. The distal occlusion device 28 and pressure-control element 38 can be advanced into vessels branched relative to each other; i.e., the distal occlusion device 28 can be positioned within a primary vessel while the distal pressure-control element 38 is positioned within a feeder vessel thereof, as discussed in detail below.

Figure 16:
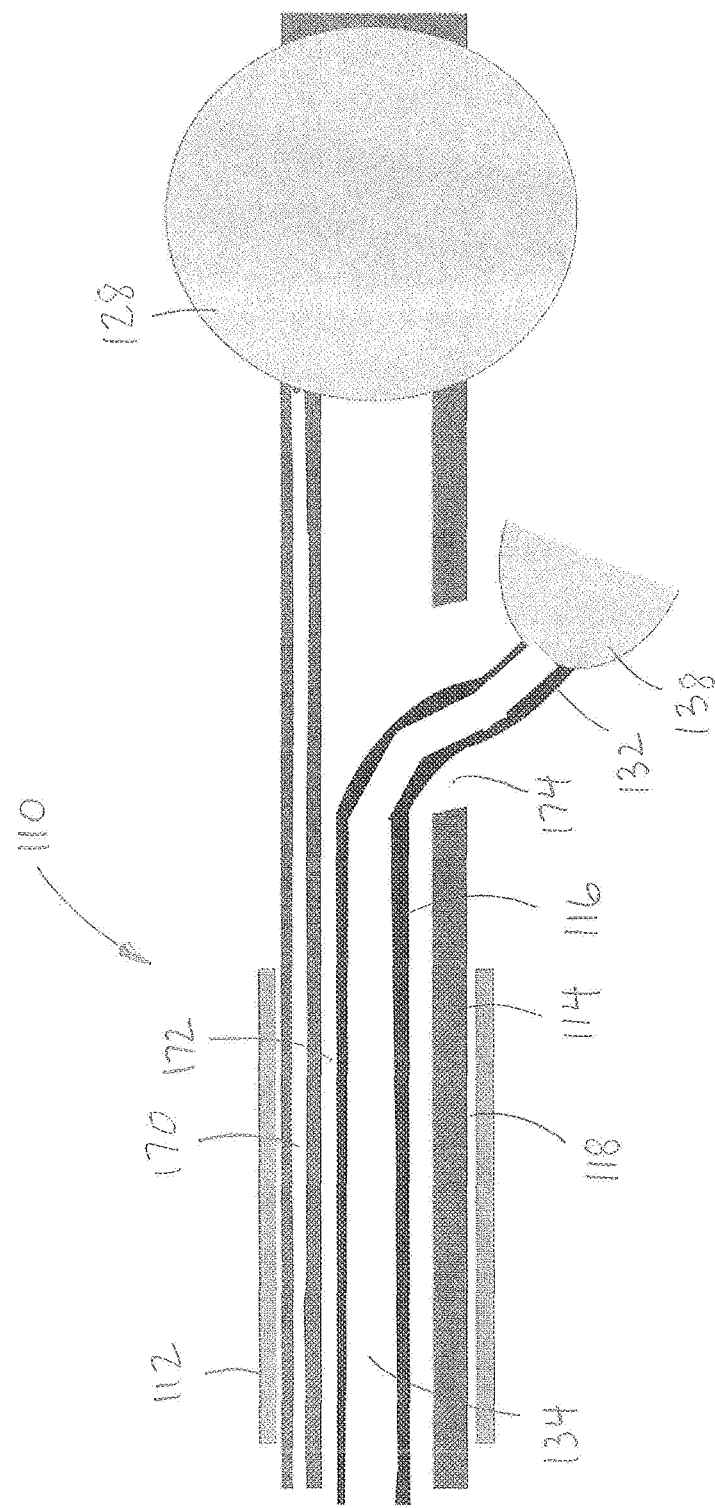
FIG. 16 is a schematic illustration of an alternate embodiment of the system in which the first and second catheters extend within a guide catheter, showing the second catheter traversing outside of the first catheter.

Turning now to FIG. 16, the distal end of an alternate embodiment of the treatment system 110 (with like parts having reference numerals incremented by 100) is shown. The treatment system includes an outer guide sheath 112, a first catheter 114, and a second catheter 116. The guide sheath 112 has a lumen 118 through which the first and second catheters 112, 114 are introduced. The first catheter includes a first lumen 170 extending to the distal occlusion device (for inflation thereof) 128, and a second lumen 172 having a side opening 174 at a location proximal of the distal occlusion device 128. The second catheter 116 has a lumen 134 extending through its distal pressure-control element 138 mounted at the distal end 132. The second lumen 172 and side opening 174 are sized to receive the distal pressure-control element 138 and second catheter 116 therethrough. The second catheter can be displaced through the second lumen of the first catheter 114 and advanced out of the side opening 174 so that the distal occlusion device 128 and pressure-control element 138 can be advanced into separate and branched vessels. The following description of the treatment system 10 equally applies to this embodiment of the treatment system 110.

In an embodiment, the occlusion device 28 on the first catheter 14 is preferably a balloon sized to be inserted into the portal vein along a portion thereof between the liver and the pancreas, and has an expanded configuration in which it is sized to extend across the splenic vein to completely block fluid flow along the splenic vein to/from the spleen.

In an embodiment, the pressure-control element 38 on the second catheter 16 includes an expanded configuration that is sized to extend across a small feeder vessel branching from the splenic vein (and thus is smaller than the occlusion device 28), and the second catheter 16 is adapted to deliver therapeutic agent through the lumen 34 and out of the orifice 36 to exit on a distal side of the pressure-control element 38. The pressure-control element 38 preferably, at least in use and optionally in design and structure, expands to a smaller maximum diameter than first occlusion device 28, as it is intended for expansion within smaller vessels (feeder vessels off of the splenic vein) than the occlusion device 28 is intended (the splenic vein itself).

The pressure-control element 38 may be a dynamic device or a static device. As shown in FIGS. 1 to 5, an embodiment of a dynamic pressure-control element includes a microvalve 38' that automatically expands to the diameter of the vessel in which it is deployed when subject to predetermined fluid pressure conditions and collapses to a smaller diameter when subject to relatively lower fluid pressure conditions. Thus, once the microvalve 38' is deployed within the vessel, the microvalve is dynamically movable (opens and closes) depending on the local fluid pressure about the filter valve: when the fluid pressure is higher on the proximal side of the microvalve, the microvalve assumes a relatively contracted configuration with a first diameter smaller than the diameter of the vessel such that fluid flow about the microvalve is permitted, and when the fluid pressure is higher on the distal side of the microvalve, the microvalve assumes an expanded configuration with a second diameter relatively larger than the first diameter in which the microvalve is adapted to contact the vessel wall. The second catheter 16 extends coaxially into or through the microvalve 38'. Radiopaque markers 44' may be provided on the catheter or microvalve to provide fluoroscopic visualization of the microvalve 38' in use. A microvalve 38' suitable for use preferably includes a filamentary braid 40' coated with a microporous polymer 42'. The microporous polymer 42' allows generation of fluid pressure at one side of the microvalve 38', while blocking particles on the pressurized side of the microvalve that exceed 5 µm from passing through the microvalve. The braid 40' preferably expands into a frustoconical form.

The braid 40' is made from metal filaments, polymer filaments, ceramic filaments, glass filaments, radiopaque oxides, or a combination of metal and polymer filaments, which are formed into a substantially frustoconical shape when not subject to outside forces. Where metal filaments are used, the filaments are preferably elastic or superelastic metal such as stainless steel or shape memory nickel-titanium alloy (Nitinol). Where polymeric filaments are utilized, the filaments may be composed of polyethylene terephthalate (PET), polyethylene-napthalate (PEN), liquid crystal polymer, fluorinated polymers, nylon, polyamide or any other suitable polymer. The polymer filaments may be impregnated with a radiopaque agent such as barium sulfate, iodine compounds, radiopaque metallic particles, or other contrast agents to facilitate imaging of the filter valve during use. Iodinated polymeric materials may also be employed as the polymeric filaments.

It is desirable that the braid 40' be biased into an expanded configuration at a predetermined force. Therefore, when polymeric filaments are utilized, one or more metal filaments may be utilized in conjunction with the polymeric filaments to provide a desired expansion force to the braid. The diameter of one, more or all of the filaments also can be selected to control the expansion force. In addition, the braid angle can be altered to change the expansion force. Further, as indicated below, the thickness of the polymer coating can be adjusted to alter the expansion force.

The radial force of expansion of a braid is described by Jedwab and Clerc (*Journal of Applied Biomaterials*, Vol. 4, 77-85, 1993) and later updated by DeBeule (DeBeule et al., *Computer Methods in Biomechanics and Biomedical Engineering*, 2005) as:

$$F = 2n\left[\frac{GI_p}{K_3}\left(\frac{2\sin\beta}{K_3} - K_1\right) - \frac{EI\tan\beta}{K_3}\left(\frac{2\cos\beta}{K_3} - K_2\right)\right]$$

where $K_1$, $K_2$, $K_3$ are constants given by:

$$K_1 = \frac{\sin 2\beta_0}{D_0} \quad K_2 = \frac{2\cos^2\beta_0}{D_0} \quad K_3 = \frac{D_0}{\cos\beta_0},$$

and $I$ and $I_p$ are the surface and polar moments of inertia of the braid filaments, E is the Young's modulus of elasticity of the filament, and G is the shear modulus of the filament. These material properties along with the initial braid angle ($\beta_0$), final braid angle ($\beta$), stent diameter ($D_0$), and number of filaments (n) impact the radial force of the braided valve.

The filaments of the braid 40' are not bonded to each other along their lengths to allow the element 38 to rapidly open and close in response to dynamic flow conditions. (The filaments may be coupled together at their proximal ends in a frustoconical construct, or at their proximal and distal ends in a tubular shape.)

As will be appreciated by those skilled in the art, the braid geometry and material properties are intimately related to the radial force and time constant of the valve. Since the valve is useful in vessels of arteries of different diameters and flow conditions, each implementation can have a unique optimization. By way of example only, in one embodiment, the element has ten filaments, whereas in another embodiment, the element has forty filaments. Preferably, the filament diameter is chosen in the range of 0.025 mm to 0.127 mm, although other diameters may be utilized. Preferably, the braid angle (i.e., the crossing angle assumed by the filaments in the fully open position—the shape memory position) is chosen in the range of 100° to 150°, although other braid angles may be used. Preferably, the Young's modulus of the filament is at least 100 MPa, and more preferably at least 200 MPa.

The polymer 42' can be coated onto the braid 40' by several methods, including by spraying, spinning, electro-spinning, bonding with an adhesive, thermally fusing, mechanically capturing the braid, melt bonding, dip-coating, or any other desired method, to form a filter. The filter can either be a material with pores such as ePTFE, a solid material that has pores added such as polyurethane with laser drilled holes, or the filter can be a web of very thin filaments that are laid onto the braid.

Where the polymer filter is a web of thin filaments, the characteristic pore size of the filter can be determined by attempting to pass beads of different diameters through the filter and finding which diameter beads are capable of passing through the filter in large quantities. The very thin filaments can be spun onto a rotating mandrel according to U.S. Pat. No. 4,738,740 with the aid of an electrostatic field or in the absence of an electrostatic field or both. The filter thus formed can be adhered to the braid structure with an adhesive or the braid can be placed on the mandrel and the filter spun over it, or under it, or both over and under the braid to essentially capture it. The filter can have some pores formed from spraying or electrospinning and then a secondary step where pores are laser drilled or formed by a secondary operation. In one embodiment a material capable of being electrostatically deposited or spun is used to form a filter on the braid, with the preferred material being capable of bonding to itself. The filter may be made of polyurethane, pellethane, polyolefin, polyester, fluoropolymers, acrylic polymers, acrylates, polycarbonates, or other suitable material. The polymer is spun onto the braid in a wet state, and therefore it is desirable that the polymer be soluble in a solvent. In the preferred embodiment, the filter is formed from polyurethane which is soluble in dimethylacetamide. The polymer material is spun onto the braid in a liquid state, with a preferred concentration of 5-10% solids for an electrostatic spin process and 15-25% solids for a wet spin process.

As another alternative construct for polymer-coating the braid, the braid can be dip-coated to form a filter onto the braid. The braid is mounted on a mandrel having the same outer diameter as the inner diameter of the fully expanded braid. The mandrel is preferably polytetrafluoroethylene (PTFE)-coated steel, in which the PTFE acts as a release surface. Alternatively, a non-coated mandrel may be used. It is important that inner diameter of the braid and the outer diameter of the mandrel not be spaced from each other when the braid is mounted on the mandrel. Thus they preferably have a common diameter within a tolerance of ±0.065 mm. Keeping the entire inner braid in contact with the mandrel allows for the filaments to be evenly coated with the polymer, as subsequently described, so that the filter valve expands uniformly after the polymer dries. Alternately, the braid can be mounted on an oversized mandrel (greater than the inner diameter of the braid), but such will result in an increase in the braid angle of the filaments, and thereby resize the filter valve and effect the expansion force thereof. In an alternate arrangement the braid may be mounted within a tubular mandrel having the same size as the outer diameter of the braid, provided with like tolerances described above. As yet another alternative, the braid can be mounted inside an undersized tubular mandrel (having an inner diameter smaller than the outer diameter of the braid), but such will result in a decrease in the braid angle of the filaments, and thereby also resize the filter valve and effect the expansion force thereof. The type of mandrel (solid or tubular), and the location of the braid thereon (external or internal), will effect localization of the polymer on the braid (providing a smooth internally coated filter valve for external mounting on a solid mandrel and providing a smooth externally coated filter valve for internally mounting within a tubular mandrel), and thereby alter areas of lubricity for the resulting filter valve.

Once the braid is tightly mounted on (or within) the mandrel, the braid is dip coated into a polymer solution at a controlled steady rate. The solution is an elastomeric thermoplastic polymer dissolved in a solvent system with a vapor point ranging from 30-200° C. to produce a solution with a dynamic viscosity range of 50-10,000 cP. The rate of decent and accent is inversely dependent upon the viscosity of the solution and ranges from 1-100 mm/sec. The rate is critical to provide an even coating of the polymer on the braid, to allow wetting of all surfaces of the braid even at locations where the braid filaments are in contact with the mandrel and consequent wicking of the polymer coating into the braid particularly to the surface in contact with the mandrel, and to release air bubbles that may be trapped during the dipping process. By way of example, in one embodiment of the method for dipping into a pellethane solution (pellethane dissolved in the solvents dimethylacetamide (DMA) and tetrahydrofuran (THF)), the rate is such that the dwell time of a 135 mm (6 inch) braid is 16 seconds. The rate is also preferably such that the polymer wicks down the length of the entire braid during withdrawal of the braid from the solution. The braid is dipped one time only into the solution to limit the thickness of the coating and thereby prevent restraint on the braid filaments and/or control smoothness of the polymer coating membrane. The controlled rate may be controlled by coupling the mandrel to a mechanized apparatus that dips and raises the braid on the mandrel at the steady and controlled rate into the polymer solution.

After the braid is withdrawn from the polymer solution, the solvent is evaporated over a time frame relative and temperature range corresponding to the solvent boiling point, with higher temperatures and longer durations utilized for high vapor point solvents. All preferred polymer solutions use some DMA to control the uniformity of the coating thickness, and may use THF to control the rate of solvent evaporation. The ratio of high vapor point solvents such as DMA to low vapor point solvents such as THF allows for control over the rate of transition from a lower viscosity high solvent content polymer solution to a high viscosity low solvent content polymer solution to a solid solvent free material, affecting the quality of the polymer membrane. In one method, the solvents are released in an oven heated to a temperature above the boiling point of DMA (165° C.) in order to rapidly release the DMA. A preferred time of heating at this temperature is 5 minutes which is sufficient to release the DMA. It is appreciated that THF has a substantially lower boiling point (66° C.) and will vaporize quickly without such substantial heating. Alternatively, the polymer-coated braid can be oven heated at a temperature below the boiling point of DMA, e.g., 80° C.-100° C., which will release of the DMA from the coated braid, but at a slower rate than would occur above the boiling point of DMA. This temperature rapidly drives off the DMA while keeping the coating braid safely below the melting or softening point of the braid. A preferred time of heating at this temperature is 10 minutes which is sufficient to release the DMA. As yet another alternative, the polymer-coated braid can be allowed to dry ambient room temperature, which results in DMA release occurring at a slower rate than each of the above.

After the solvents have been released from the polymer-coated braid, the coated braid is cooled below the glass transition temperature of the polymer to plasticize the polymer on the braid. Once cooled, the coated braid is released from the mandrel. If the mandrel is coated with PTFE, the braid may self-release from the mandrel or may be readily released. If the mandrel is uncoated, a release agent such as isopropyl alcohol (IPA) may be used to facilitate removal of the coated braid from the mandrel. The resulting elastomeric membrane filter formed on the braid may be elastically deformed over a range of 100-1000% elongation. In addition to pellethane, the membrane may be formed from, but not limited to, other thermoplastic elastomers including other urethanes such as aliphatic polyether-based thermoplastic polyurethanes (TPUs), and styrene-isoprene-butadiene-styrene (SIBS). These polymers may be dissolved in appropriate solvents or heated to their melting point to form a fluid.

By way of example, various embodiments of microvalves suitable for use as a dynamic pressure controlled element 38' are disclosed in co-owned U.S. Pat. No. 8,696,698 and co-owned US Pub. Nos. 20150272716 and 20150306311, which are hereby incorporated by reference herein in their entireties.

A static pressure-control element 38" can be actuated to expand or can be self-expanding. The static element 38" can comprise a fluid inflatable balloon 40" (FIGS. 6 and 7), a self-expanding (non-dynamic) filter 40''' (FIG. 8), or a mechanically expandable device 40'''', such as a malecot (FIG. 9). Each of these static elements 38" can occlude a vessel by being sufficiently expanded to block flow within the vessel around the static pressure-controlled element, and do not modulate in size in view of localized fluid pressure conditions within the vessel and about the element 38". Similarly, the static element 38" can also include radiopaque markers 44" to fluoroscopically identify its location within the vessel.

Referring to FIG. 10, the system may also include an access needle 50 provided with a proximal opening 52, a distal opening 54, a lumen 56 therebetween, and a piercing tip 58. The access needle 50 is preferably curved. The piercing tip 56 may be at the end of a removable obturator 60, which when removed exposes the distal opening 54. The piercing tip 56 is configured and sized to directly pierce a vessel, and particularly the portal vein, and enter into the interior of the portal vein in a manner that communicates the distal opening 54 of the access needle with the interior of the portal vein. In an embodiment, the access needle includes a lumen sized to permit longitudinal passage of the guide sheath 12 therethrough. The system may also include an exchange device (not shown) to facilitate displacement of the access needle 50 over the guide sheath 12, particularly after the guide sheath has been inserted into the portal vein, as described hereinafter.

Figure 20:
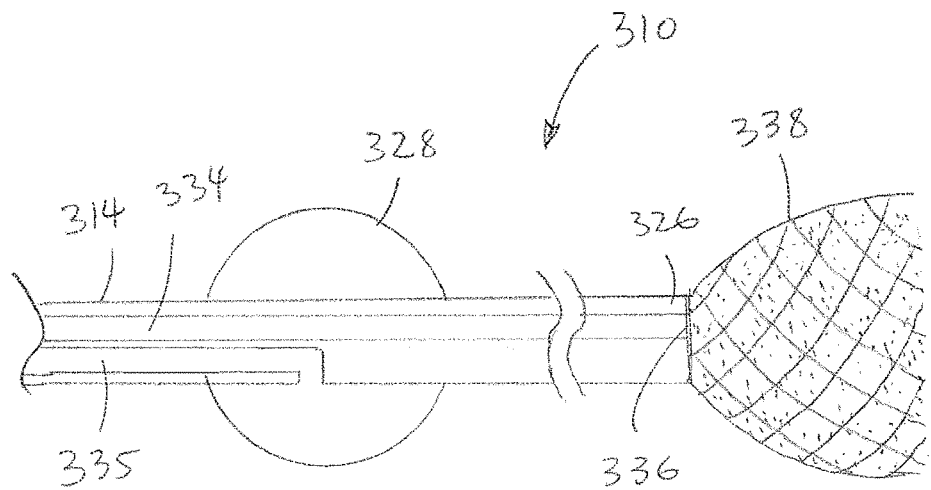
FIG. 20 is a schematic illustration of yet another embodiment of a distal end of a treatment system for performing pressure-controlled therapeutic delivery.

Referring to FIG. 20, another embodiment of the system 310 includes a catheter 314 having first and second lumens 334, 335. A dynamic or static first occluder 338 is provided to the catheter 314 adjacent the distal end 326 of the catheter. A static second occluder 328 is provided to the catheter 314 proximally displaced relative to the first occluder 338. The first lumen 334 is in fluid communication with a distal orifice 336 at the distal end 326 of the catheter and which opens into the first occluder 338, and the second lumen 335 is in fluid communication with the second occluder 328, and adapted to cause expansion of the second occluder 328 when a sufficient volume of fluid is injected therein.

Figure 21:
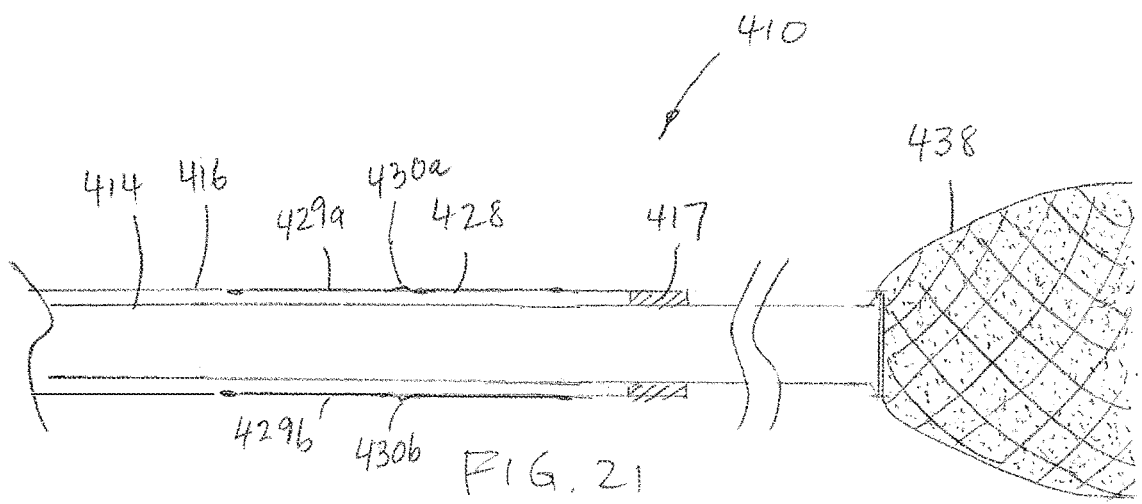
FIG. 21 is a schematic illustration of still a further embodiment of a distal end of a treatment system for performing pressure-controlled therapeutic delivery, with a second occluder shown in a collapsed configuration.
Figure 22:
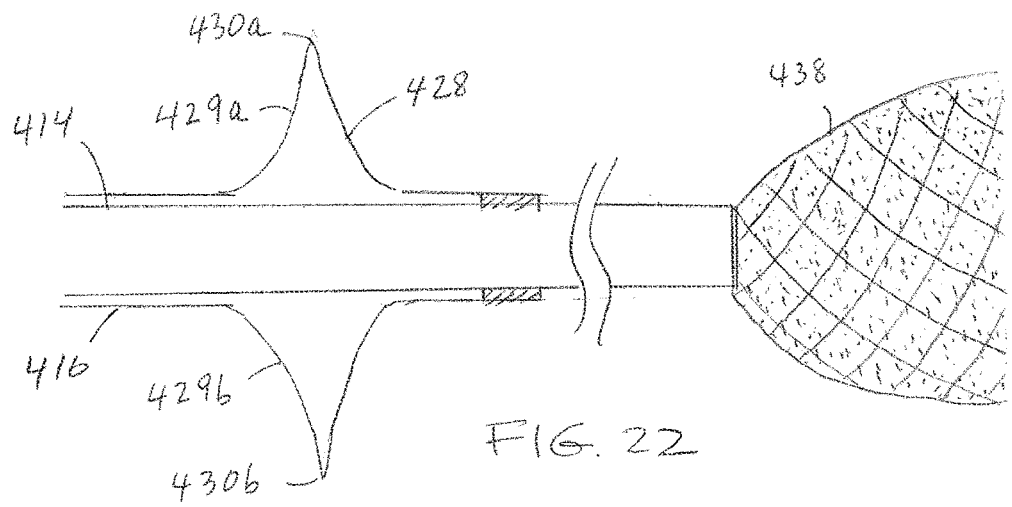
FIG. 22 is a schematic illustration of the embodiment of the treatment system of FIG. 21, with the second occluder shown in an expanded configuration.

Turning now to FIG. 21, in another embodiment of the system 410, the first and second catheters 414, 416 extend coaxially, one within the other. The dynamic occluder 438 is provided at the end of the first catheter 414, and the second occluder 428 (shown in a collapsed configuration) is provided at the end of the second catheter 416. The second occluder 428, in the form of a mechanically expandable malecot, defines a plurality of radially expandable flaps 429a, 429b (two flaps shown in this view, but additional flaps are intended as shown in FIG. 9) that can each bend at a hinge point 430a, 430b. The distal end of the second catheter 416 is fixed relative to the first catheter 414, for example, with a crimp collar 417. Referring to FIG. 22, when the first catheter 414 is retracted relative to the second catheter 416, the second occluder 428 expands.

Figure 17:
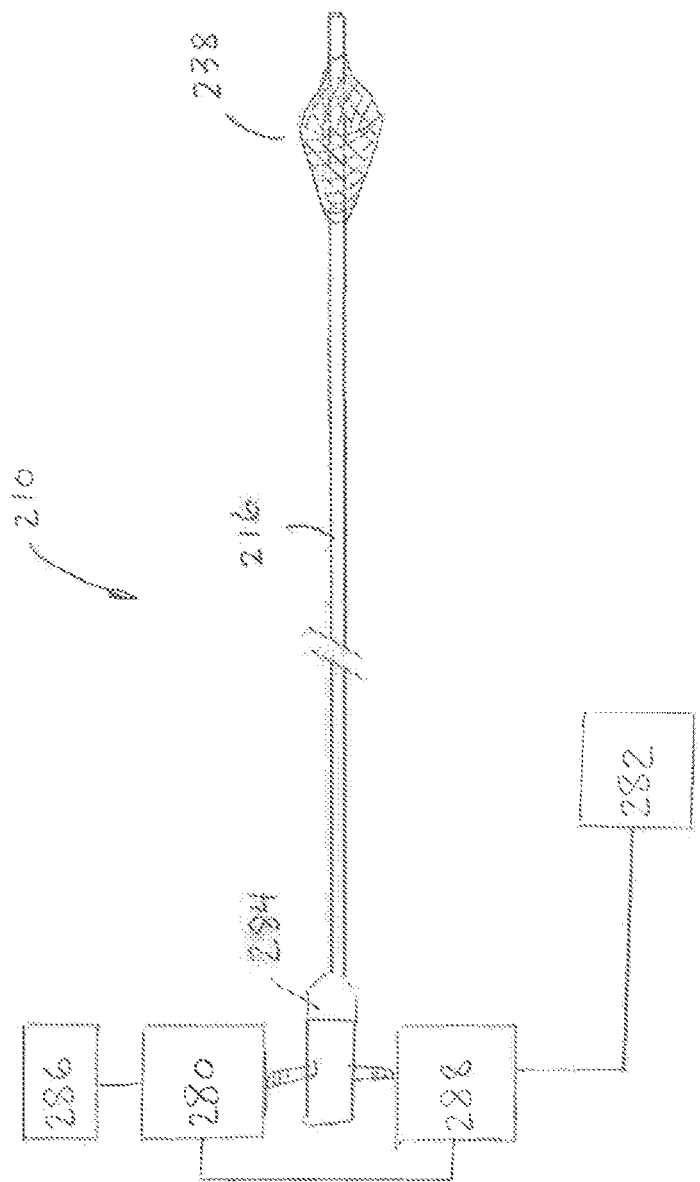
FIG. 17 is a schematic illustration of another embodiment of a treatment system for performing pressure-controlled therapeutic delivery.

Turning now to FIG. 17, another embodiment of the system 210 is shown. The system 210 includes a catheter 216 having a pressure control element 238 at its distal end. The system further includes an internal pressure-detecting element 280 and/or an external, pressure-responsive, timing element 282 adapted to permit injection of the infusate based on a localized pressure or a timing event correlated to pressure. The pressure-detecting element 280 can be coupled to the proximal or distal ends of the catheter 216, or provided as other structure for co-delivery with the catheter 216 or separate guidance to a suitable location at which pressure is advantageously sensed. The infusion timing element 282 can be coupled to the system directly or wirelessly. The system 210 is further provided with an outer guide sheath and access needle, as previously described with respect to guide sheath 12 and needle 50. The system 210 may optionally be provided with another catheter having another distal occlusion device, as previously described with respect to catheter 14 and occlusion device 28.

The pressure-detecting element 280 can be a pressure sensor or other system that detects the pressure in the heart or at the target organ. The pressure-detecting element 280 may be coupled at the proximal end of the 216, e.g., at a multi-port hub 284, but is in communication with the distal end of the catheter 216 and identifies to the user the local pressure thereat. The identification may occur with a meter or display 286 coupled to the pressure-detecting element 280. This permits injection of the infusate during an intended blood pressure; change in blood pressure; or at a prescribed time delay relative to a change in pressure at the heart or in the target organ. The pressure-detecting element 280 can, e.g., permit or activate infusion during the diastolic period and halt or deactivate infusion during the systolic period; this increases the pressure differential in the target organ and maximizes organ uptake of the infusate.

Additionally, the pressure-detecting element 280 may be optionally coupled to a pump 288 that automatically injects the treatment agent through the multi-port hub 284 upon detection of the pressure condition. As the pressure events may cycle quickly, automation of the infusion upon the detected pressure condition removes the human response time as a limitation in rapidly responding to the detected pressure condition. Moreover, the pump 288 can be operated to modify the rate of infusion in a closed loop fashion to produce an intended pressure value during administration of the therapy.

In an embodiment, the pressure-responsive, infusion timing element 282 is adapted to permit injection of the infusate via the pump 288 at a set time offset following a portion of the cycle of the heart rate, with such delay capable of accounting for a consequent change in pressure occurring in the target organ after a pressure change at the heart. By way of example, the timing element may include a connection to an EKG or a pulse-oximeter.

Figure 12:
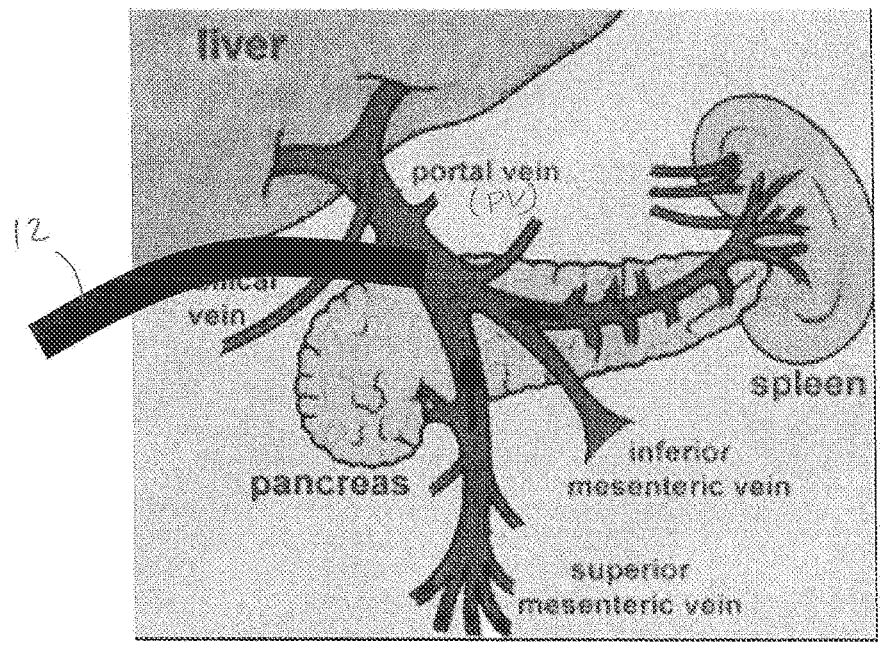

Turning now to FIG. 11, in one method of use described with respect to system 10 (but generally applicable to systems 110 and 210), the access needle 50 is deployed into a primary vessel from which feeder vessels extend or into a vessel adjacent and directly communicating with the primary vessel. By way of example, for treatment of feeder vessels extending from the splenic vein (SV), the access needle 50 is inserted directly into the adjacent portal vein (PV), preferably without traversing other endovascular vessels, which can be achieved by directly puncturing the portal vein with the aid of ultrasound visualization. Then, as shown in FIG. 12, the guide sheath is inserted through the access needle and into the portal vein, and the access needle is withdrawn, leaving the guide sheath in position within the portal vein (PV). Alternatively, the exchange device (not shown) is used to replace the access needle with the guide sheath. Regardless, the guide sheath 12 may be advanced into the portal vein (PV). The first and/or second catheters 14, 16 may be preloaded in the guide sheath 12 and preferably advanced toward the distal end 22 of the guide sheath (as shown in FIG. 2). Alternatively, the guide sheath 12 may be advanced empty of the first and/or second catheters 14, 16, with such catheters advanced together thereafter or individually as necessary. As yet another alternative, the guide sheath 12 may be advanced with the first and/or second catheters 14, 16 partially advanced within the guide sheath. In accord with alternate methods using both first and second catheters 14, 16, the first catheter 14 is advanced to the distal end of the guide sheath after the guide sheath is situated in the portal vein (PV).

Figure 13:
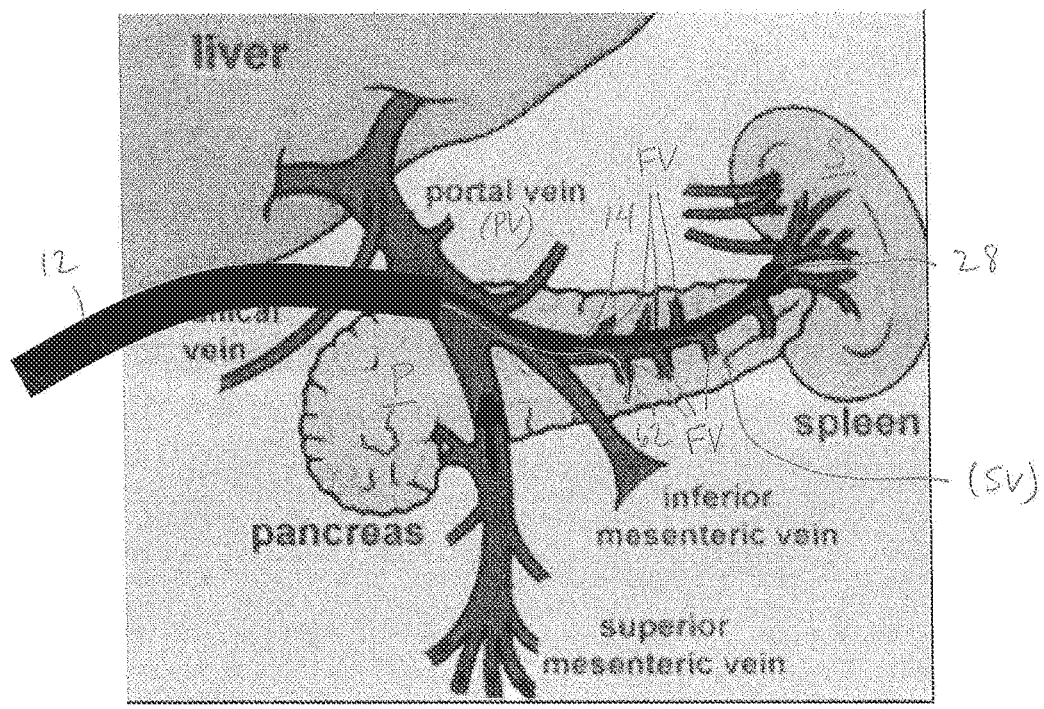

Referring to FIG. 13, in accord with one method, the first, static occlusion element 28 at the distal end of the first catheter 14 is then advanced out of the guide catheter 12, through the portal vein (PV) and into the splenic vein (SV) traversing the pancreas (P) and to the origin of the spleen(S). Once the static occlusion element 28 is at the end of the splenic vein (SV) adjacent the spleen(S), the static occlusion device 28 is expanded, e.g., via fluid inflation along the first catheter 14, to occlude portal venous flow into the spleen.

A large bolus of contrast agent is then injected into the portal vein (PV) and through the splenic vein (SV) to image the portal and splenic vein anatomy. Preferably, the contrast agent is injected through the guide catheter 12 (either through lumen 18 shown in FIG. 3 and around the first and second catheters, or within a dedicated lumen thereof); less preferably, the contrast agent may be injected through holes in the first catheter located proximal of the first occlusion element, however, the volume and pressure will not be as preferable as injection through the larger diameter guide catheter. The contrast agent is prevented from entering the spleen(S) by the static occlusion element 28, and therefore is targeted to the splenic vein (SV) and feeder vessels (FV) extending off of the splenic vein (SV) and deep into the pancreas (P). The static occlusion element 28 may then remain in the expanded state, or optionally is contracted via deflation to again permit blood flow between the spleen(S) and the portal vein (PV).

A guidewire 62 is then advanced through the guide catheter 12, under guidance of the visualization provided by the contrast agent, and guided into a first feeder vessel extending from the splenic vein. The guidewire 62 is a microwire, preferably 0.014-0.020 inch. Using the first embodiment of the treatment system 10, the guidewire is advanced parallel and non-coaxial to the first catheter; using the second embodiment of the treatment system 110, the guidewire is advanced through the first catheter and out of its side opening 174 (FIG. 16).

Figure 14:
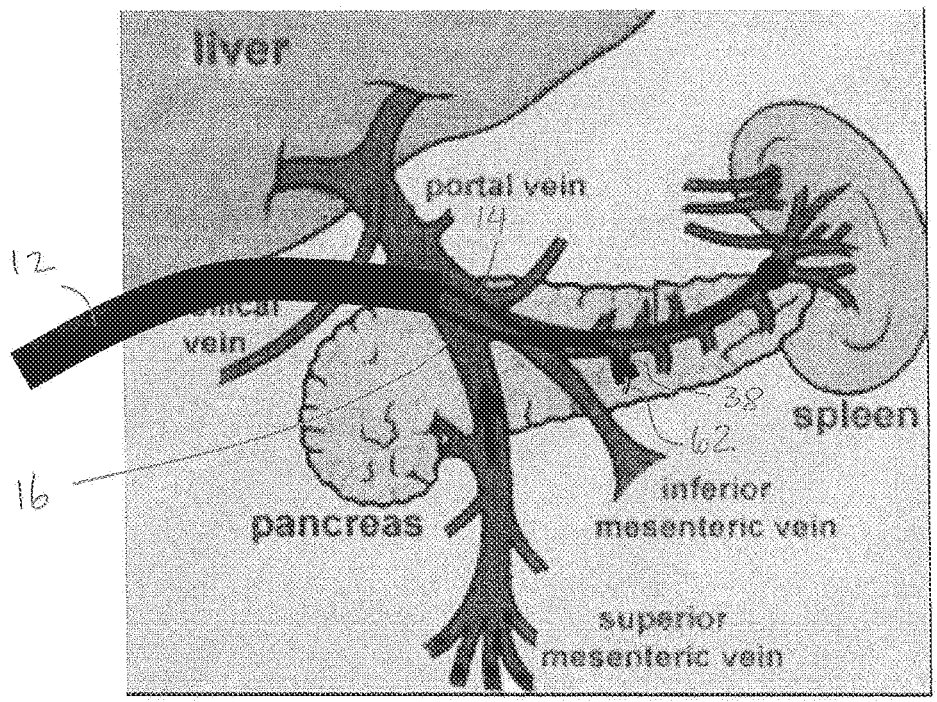

Turning to FIG. 14, the second catheter 16 is then advanced over the guidewire 62 so that the second occlusion device 38 is at or beyond the ostium of the first feeder vessel. If the second occlusion device is a static device 38", 38''', 38'''', it is then expanded to block fluid passage within the first feeder vessel. If the second occlusion device 38' is dynamic, no pre-expansion to the feeder vessel wall is required, as the second occlusion device will automatically expand thereto when subject to the increased fluid pressure of the injected treatment agent. The treatment agent is then injected under pressure through the second catheter 16, distally of the second occlusion device 38, and into the feeder vessel. The treatment agent is preferably injected in combination with a contrast agent to monitor the progress of tissue penetration. With such pressure, preferably the treatment agent is forced deep into hypoxic regions of tissue which are not serviced by circulating blood flow. Thus the treatment can reach tissue not serviced by other treatment methods and remains in the tissue to be effective for a relatively long period of time.

Depending on the type of treatment agent, different infusion procedures are preferably utilized. For a 'heavy' infusate, such as radioembolization spheres, the agent is infused from outside the body through the second catheter 16 at a relatively high pressure, e.g., 300-1200 psi, in order to drive the spheres forward within the second catheter 16 and vessels as fast as possible so that the spheres do not settle out of suspension and deliver before reaching the target tissue, i.e., tumor. The infusion pressure preferably generates a net increase in fluid pressure within the vessel of 10 mmHg to 200 mmHg above systemic pressure. A 'heavy' infusate would substantially reflux if infused through a traditional microcatheter. The second catheter 16 and second occlusion element 38 are capable of supporting rapid increases in pressure, on the order of milliseconds, which is required in such procedures. Such an infusion procedure may result in the development of high shear rate conditions, which is not an issue for a 'heavy' infusate.

For various biologic infusates, particularly cells such as CAR-T, CAR-NK, TCR-R, TCR-NK, and B-cells or combinations thereof, relatively lower shear rates are desired to prevent damage to the cells and/or to prevent premature activation of the cells. Therefore, a different method is preferred. The cells are infused from outside the patient through the second catheter 16 at a relatively low pressure, e.g., below 300 psi, and after the cells are out of the second catheter and into the feeder vessel, where there is a lower shear rate, a bolus of saline is flushed through the second catheter at a significantly higher pressure (above 300 psi) to promote distal flow of the biologic infusate deep into the tumor and support forward flow of the infusate from the feeder vessel into newly opened regions of the tumor and/or tissue. The two steps of infusing the biologic and then flushing can be repeated.

Referring back to FIG. 6, in one embodiment for biologic infusion, the proximal end of the second catheter 16 includes a hub 90 coupled to first and second ports 92, 94 at a two-way stopcock 96. The first port 92 is intended to receive the biologic infusate, and the second port 94 is intended to receive the saline. The stopcock 96 is first set to communicate the first port 92 with the second catheter 16, and the biologic infusate is infused at relatively low pressure. The stopcock 96 is then reconfigured to communicate the second port 94 with the second catheter 16, and the second catheter is flushed in accord with a desirable pressure and time profile. For example, the second catheter 16 may be flushed at a relatively low pressure with 2 mL to clear remaining biologic infusate from the second catheter, and then flushed with 20 mL at a relatively higher pressure of 1200 psi; or may be cycled up and down between 300 to 2000 psi; other suitable profiles for infusing the biologic infusate and the saline flush at relatively different pressures can be used. The infusion of the biologic infusate followed by saline is preferably repeated to promote deep penetration of the biologic infusate into the tissues. The infusion and flush through the second catheter may be effected manually or via a pump.

Optionally, the infusion pressure can be measured after each infusion in order to monitor the infusion pressure relative to systemic pressure. More particularly, a standard sphygmomanometer or other blood pressure monitor can be used measure systemic patient blood pressure. Then, a blood pressure monitor coupled to the hub of the second catheter is utilized to measure pressure at the infusion target. The treatment agent is infused until the infusion target measures systemic pressure, 10 mmHg above systemic pressure, or 200 mmHg above systemic pressure.

Figure 31:
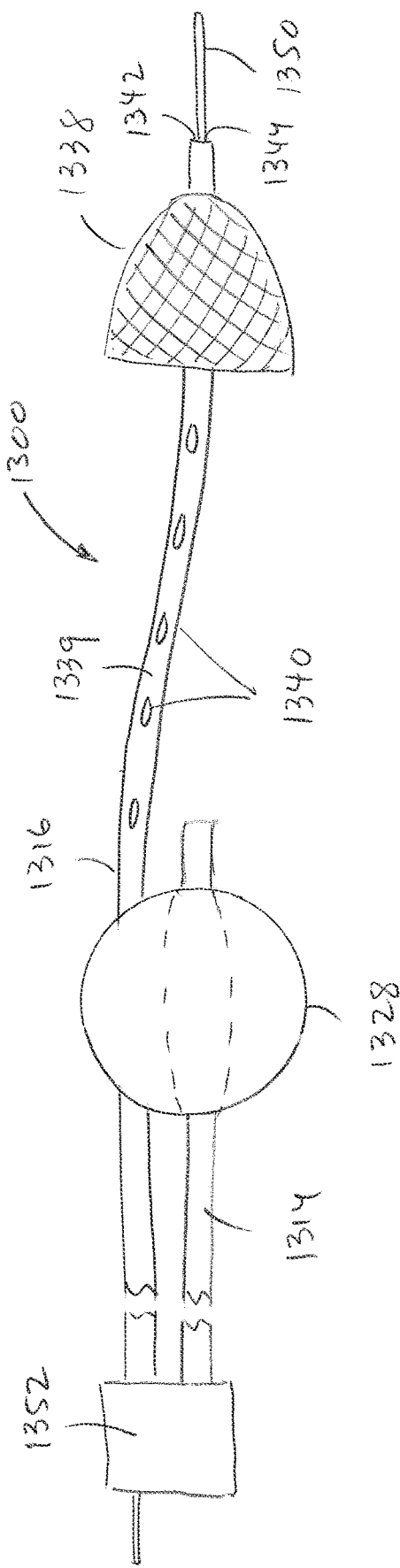
FIGS. 31, 32 and 33 are schematic illustrations of alternative embodiment of a pressure-controlled therapeutic treatment system.

Turning now to FIG. 31, another embodiment of a system for use in the treatments described herein is shown. The system 1300 includes a first catheter 1314 having at its distal end a static occlusion device 1328, and a second catheter 1316 having at its distal end a dynamic occlusion device 1338. In distinction from prior embodiments, the dynamic occlusion device 1338 is reversed in direction such that it is attached only a relatively distal location on the second catheter 1316 and is expandable outward to a larger diameter at a location relatively proximal of its attachment. In addition, a distal portion of the second catheter 1339, proximal of the dynamic occlusion device includes a plurality of radial holes 1340 in communication with a first lumen of the second catheter. The first lumen of the second catheter has a closed distal end 1342. The second catheter 1339 may also include second lumen with an open distal end 1344 for passage of a guidewire 1350. When used as a system inside the body, the second catheter 1316 may be longitudinally displaceable relative to the first catheter 1314 to define a variable distance between the static occlusion device 1328 and the dynamic occlusion device 1338, with the radial holes located therebetween. The proximal ends of the first and second catheters are coupled to a hub 1352.

Figure 32:
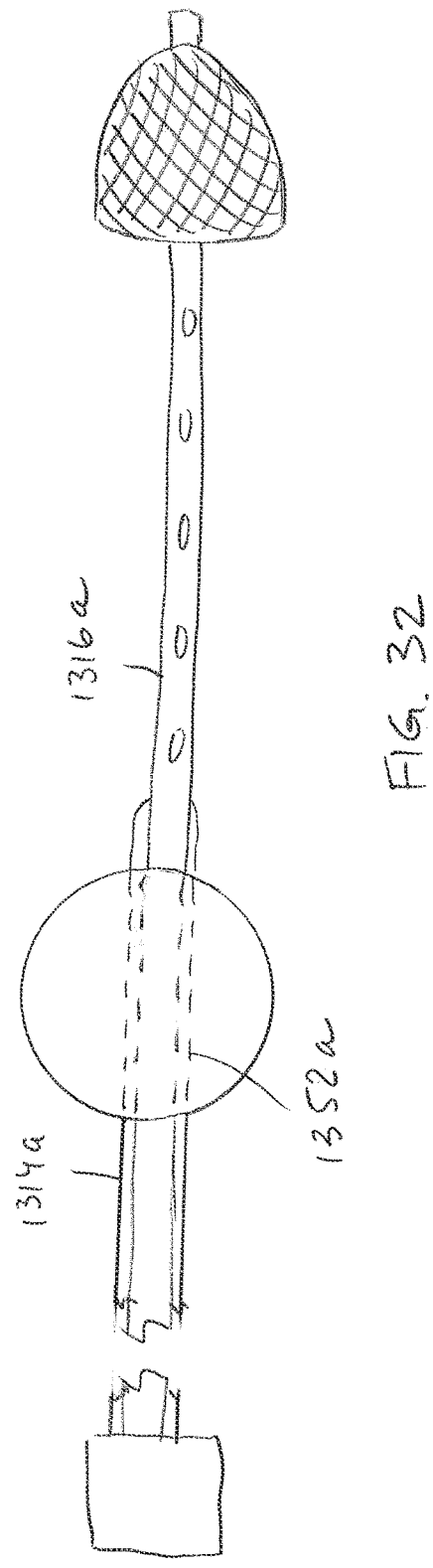

In embodiments, the first and second catheters can be longitudinally displaced relative to each other. In one embodiment, the first and second catheters are separate from each other, and may extend parallel to each other, as shown in FIG. 31. In another embodiment, the second catheter 1316a may extend through a third lumen 1352a in the first catheter 1314a, as shown in FIG. 32.

In yet another embodiment, the static occlusion device 1328b and dynamic occlusion device 1338b are fixed in relatively displaced positions along a single catheter 1314b, with the radial holes 1340b provided in the catheter 1314b between the static occlusion device 1328b and dynamic occlusion device 1338b. The positions of the static occlusion device 1328b and dynamic occlusion device 1338b are designed to accommodate a fixed distance between anatomical landmarks such as the branch of the interior mesenteric vein and the spleen. This embodiment may also be provided in different sizes to accommodate different anatomical distances as well as to accommodate different procedures carried out in and with respect to different organs, tissues and vessels.

Figure 33:
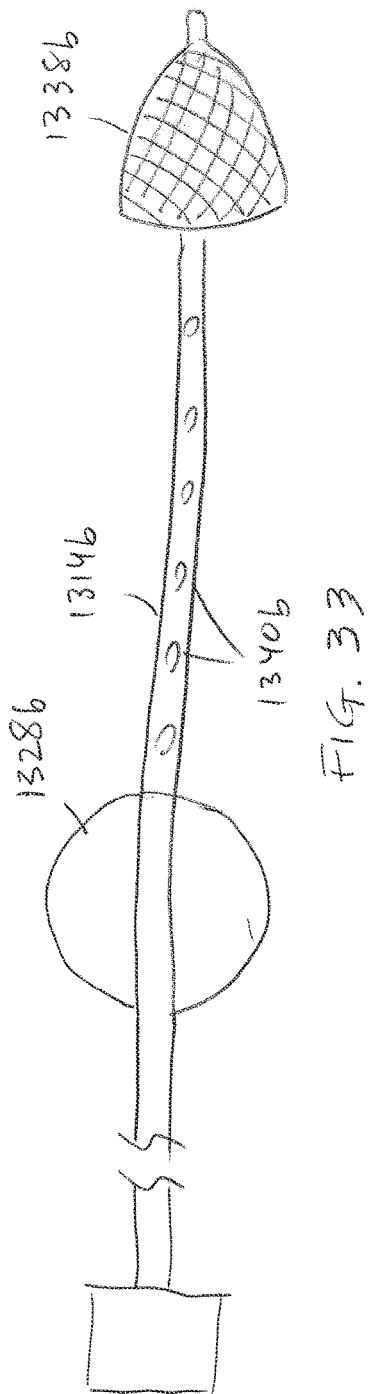
Figure 34:
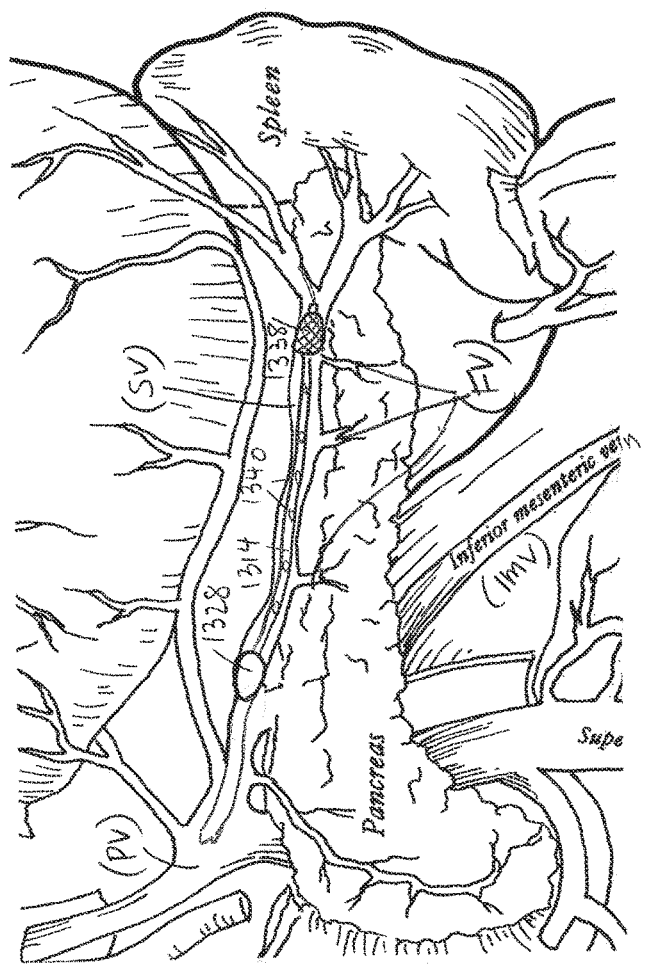
FIG. 34 illustrates a method of using the embodiments of pressure-controlled therapeutic treatment systems in FIGS. 31, 32 and 33 to perform a venous-side therapeutic treatment procedure in the splenic vein.

Turning to FIG. 34, in one method of use, the first and second catheters 1314, 1316 are advanced through the portal vein (PV) and into the splenic vein (SV), with the static occlusion device 1328 positioned just distal of the branch of the inferior mesenteric vein (IMV), and the dynamic occlusion device 1338 positioned just proximal of the spleen. The feeder vessels (FV) extending from the splenic vein (SV) are located between the two occlusion devices 1328, 1338. An inflation medium such as saline is then injected into through the first catheter 1314 and into the static occlusion device 1328 to sufficiently expand the static occlusion to block flow within the vessel past the static occlusion device 1328. Then, a treatment agent is injected under pressure through the first lumen of the second catheter 1316 and out of the holes 1340 into the splenic vein (SV) between two occlusion devices 1328, 1338. As the treatment agent exits the holes 1340, the pressure within the splenic vein (SV) increases beyond the natural blood pressure such that there is higher pressure on a proximal side of the dynamic occlusion device 1338 (facing the feeder vessels (FV)) than the distal side of the dynamic occlusion device (facing the spleen). This causes the reverse-oriented dynamic occlusion device 1338 to expand under the increased pressure and block flow of the treatment agent from flowing distally of the dynamic occlusion device 1338 and toward the spleen. Therefore, the treatment agent is forced under pressure into the feeder vessels (FV). Once infusion of the treatment agent is completed, the pressure equilibrizes on the proximal and distal sides of the dynamic occlusion device 1338 and the dynamic occlusion device 1338 at least partially automatically collapses again permitting flow thereby. A similar procedure can be accomplished with the single catheter embodiment shown in FIG. 33.

Figure 18:
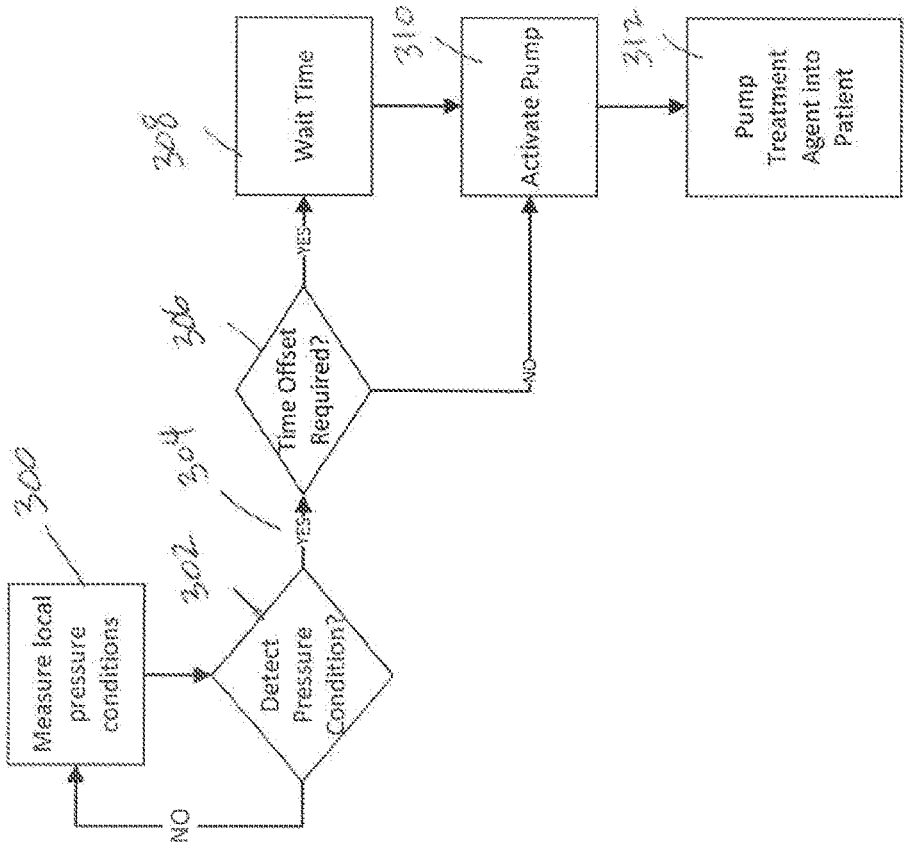
FIG. 18 is a flow chart of a method of using a system described herein.

Referring now to FIG. 18, in accord with another method for infusion of a treatment agent, a system may be provided in accord with system 210 of FIG. 17 and advanced into the patient. The system 210 can include both internal, pressure-detecting element 280 and external, pressure-responsive, timing element 282, or the pressure-detecting element without the timing element. At an appropriate point in the procedure, the pressure-detecting element 280 is operated at 300 to detect a pressure condition at the target location for infusion or another local condition within the patient, e.g., at the heart. The system continually monitors for such condition at 302 until such condition occurs at 304. Upon detection of the pressure condition at 304, the system determines at 306 whether a time offset has been set to delay injection of the treatment agent for a preset period of time after detection of the pressure event. If a time offset has been set at 306, the system waits the time offset at 308. Then, after the delay at 308, the pump is activated at 310 to infuse at 312 a determined amount of treatment agent into the patient. If no offset has been set at 306, the system immediately activates the pump at 310. The method includes infusing a full dose of the treatment agent at 312, or alternatively infusing a partial dose of the treatment agent. A defined portion of the dose can be infused during each of several pressure conditions being met. For example, for a treatment dose of 100 mL, four partial doses each of 25 mL may be infused, each upon the detection of the preset pressure condition.

Figure 19:
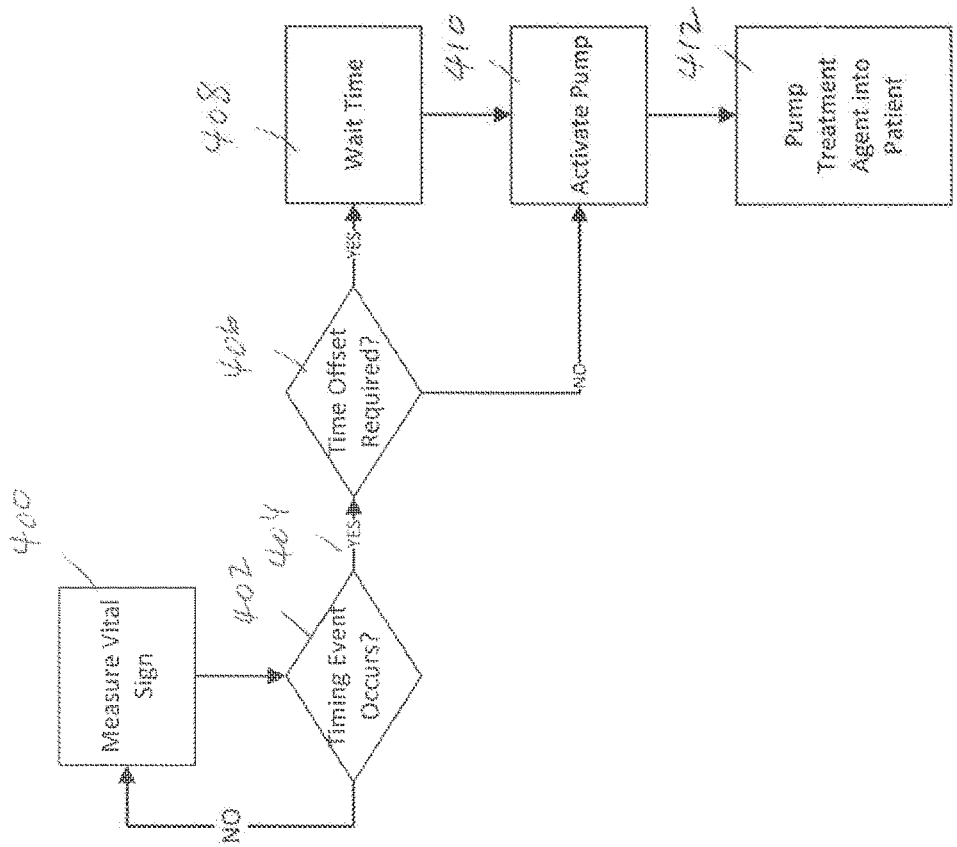
FIG. 19 is another flow chart of a method of using a system described herein.

Referring now to FIG. 19, in accord with another pressure-responsive method for infusion of a treatment agent, a system may be provided in accord with system 210 of FIG. 17 and advanced into the patient. The system can include both intravascular pressure-detecting element 280 and timing element 282, or the timing element 282 without intravascular pressure-detecting element. At an appropriate point in the procedure, the timing element 282 is operated 300 to measure vital signs of the patient. Such vital signs may be measured externally of the patient and does not require direct monitoring of pressure within the patient's system. However, the vital sign measured is correlated to the patient's pulse and thus reliably indicates pressure events occurring within the vascular system of the patient. By way of example, a pulse oximeter or an EKG can be used as the timing element. The system continually monitors for a timing condition at 402 until a suitable timing condition is detected at 404. Upon detection of the timing event at 404, the system determines at 406 whether a time offset has been set to delay injection of the treatment agent for a preset period of time after detection of the timing event. If a time offset has been set at 406, the system waits the time offset at 408. Then, after the delay at 408, the pump is activated at 410 to infuse at 412 a determined amount of treatment agent into the patient. If no offset has been set at 406, the system immediately activates the pump at 310. The method includes infusing a full dose of the treatment agent at 412, or alternatively infusing a partial dose of the treatment agent. It is appreciated that even though the system measures vital signs external of the vascular system, it is adapted to pressure-responsive to the intravascular pressure.

The methods described with respect to FIGS. 18 and 19 can be used separately or can be combined where both a pressure-detecting element and a timing element are incorporated into the system.

Regardless of the method, infusion preferably continues until either the target dose is infused, enhancement of downstream non-target collateral vessels is realized through visualization, or a target pressure is reached.

At the conclusion of infusion through the second catheter 16 within the feeder vessel, the second occlusion element 38, 138 is collapsed (or, in accord with alternate embodiments, the only occlusion element 238 is collapsed). As an option, while the second occlusion element 38, 138, 238 is deployed within the feeder vessel and before it is collapsed, the vessel is slowly aspirated to relieve pressure and prevent backflow of infusate. Once the second occlusion element is collapsed, the treatment agent may begin to travel through the splenic vein and enter the portal vein. Therefore, saline is again further infused through at least one of the second catheter and the guide catheter to dilute the treatment agent as the treatment agent begins systemic circulation.

Figure 15:
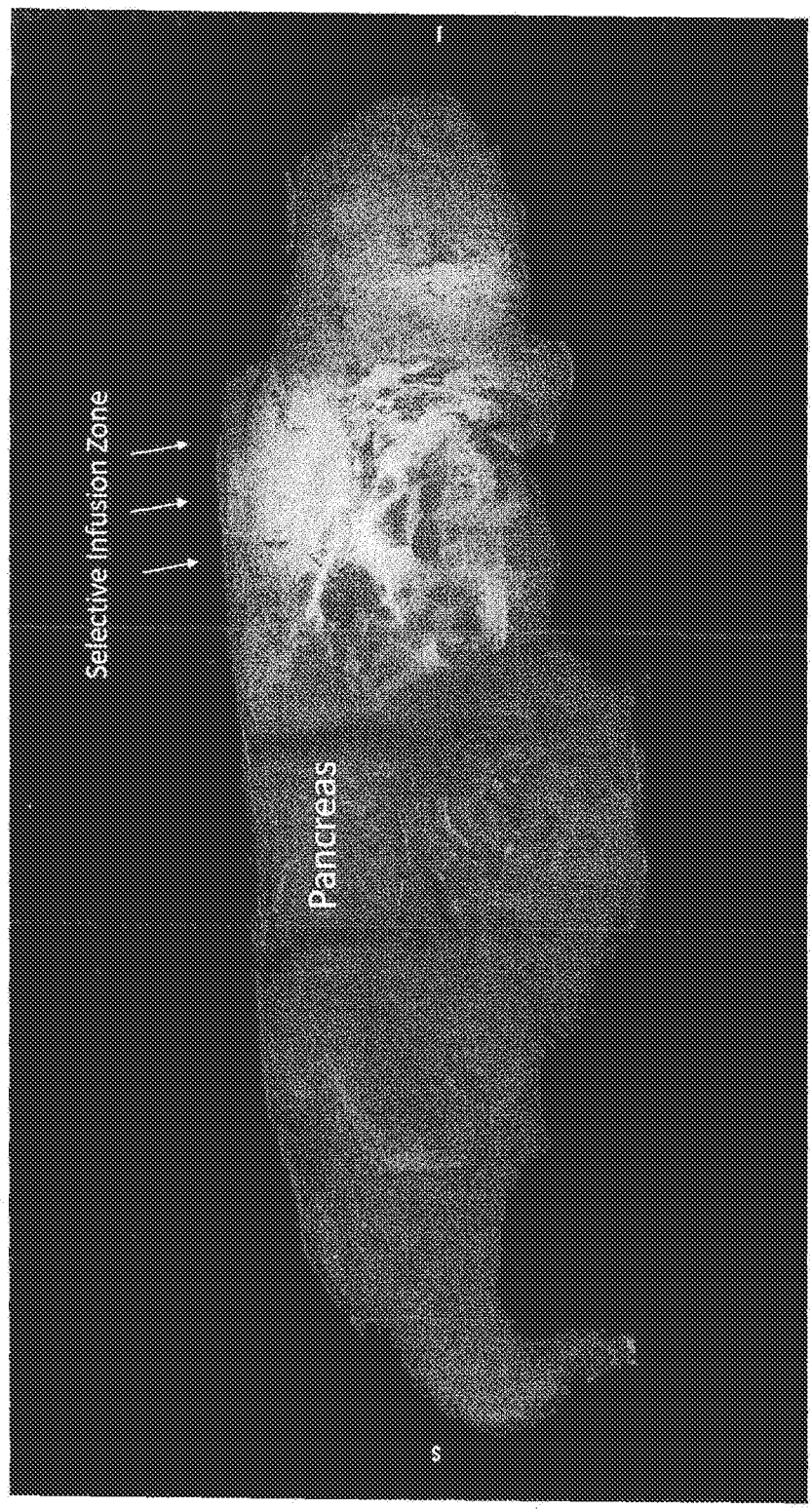
FIG. 15 is a photograph showing exemplar results of treatment by pressure-controlled therapeutic delivery on a porcine pancreas.

The treatment may then be continued by advancing the guidewire 62 into a different second feeder vessel, the second catheter over the guidewire into the second feeder vessel and providing an additional portion of the dose of the treatment agent under pressure into the second feeder vessel. The process may be repeated until an appropriate dose has been infused to selected target tissue through the one or more of the feeder vessels. After the infusion is completed, the first and second catheters and guide catheter are then withdrawn from the portal vein and out of the patient. Turning to FIG. 15, a porcine pancreas infused in accord with the described methods is shown, with the highlighted area illustrating the depth of penetration obtained by the infusate using methods described herein.

The system, as indicated above, can be used without the first catheter and occlusion element 28; infusion is effected through and out the distal orifice of the second catheter alone. The pressure-detecting element and/or infusion timing elements are consequently coupled to the second catheter.

The system and procedures described herein provide several advantages over known prior art. Relative to a system including two coaxial balloons (or two filters), the treatment system and methods herein provide precise, targeted infusion of the treatment agent. In addition, the treatment system and method allow high-pressure infusion permitting the treatment agent to extend deeper into target tissues and even open up vessels that may be otherwise closed to treatment. This is, at least in part, because infusion is presented at the end of the system and because the system as used in the method permits pressure control. It should be understood that it is not feasible to generate significant pressure to overcome tumor pressure in large cross-sectional vessels, such as the portal or splenic veins in view of the size of the catheter used in prior devices. In order to achieve significant injection pressures measured at the hub of the second catheter, a preferred and suitable ratio of catheter inner diameter to vessel diameter is 1:8; i.e., a 0.021 inch inner diameter catheter is well suited for 0.168 inch vessel. In addition, the dynamic second occlusion element 38" automatically dilates as the pressure increases; this permits, e.g., up to a three times an increase in diameter relative to an initial diameter automatically in response to local pressure conditions resulting from the infusion of the treatment agent. Moreover, the dynamic second occlusion element 38" is both a filter and a valve. The filter allows flow of plasma and contrast agent to provide an indication of the local flow conditions to the interventionalist. The valve dynamically expands substantially immediately during deployment to trap reverse flowing blood and rapidly reaches arterial systemic mean pressure. The valve operates to occlude the feeder vessel, and as pressure increases and the vessel seeks to expand, the valve increases occlusion. In distinction, a balloon becomes less occlusive as the pressure increases and the vessel expands.

While the above systems and methods have been described particularly with respect to treatment of the pancreas, the systems and methods can clearly be used in a similar manner to provide treatment of other organs and tissues.

By way of example, the systems and methods can be used in the treatment of prostate cancer. The prostate can be approached from either arterial access or venous access. In an arterial approach, the prostate can be approached from either the femoral or radial arteries. In a femoral approach, the iliac artery is accessed from the femoral artery using standard methodology. The catheter with occluder(s) is then tracked to the internal iliac artery, then to the vesical artery, and then to the prostatic artery. In a radial approach, the radial artery is accessed using standard methodology. The catheter with occluder(s) is then tracked through the radial artery, to the brachial artery, to the axillary artery, to the subclavian artery, to the aortic arch, and then to the descending aorta. From there, tracking is continued to the iliac artery, to the internal iliac artery, to the vesical artery, and then to the prostatic artery. In a venous approach, the femoral vein is accessed followed by selective cannulation of the internal iliac veins and prostatic veins of the pelvis. Regardless of the approach, once the occluder is positioned in a vessel in close fluid communication with the prostate, at least one occluder is expanded prior to and/or substantially simultaneously with the infusion of the treatment agent to constrain the flow of the treatment agent, and generate elevated downstream pressure of the occluder that creates deep penetration of the vessels of the prostate with the treatment agent.

By way of another example, the systems and methods can be used in the treatment of thyroid cancer. The thyroid can be approached from either arterial access or venous access. In arterial access, the thyroid can be approached from at least the femoral or radial arteries. In a femoral approach, the iliac artery is accessed using standard methodology. The catheter with occluder(s) is then tracked to the aorta, and then to the aortic arch. From there, the inferior thyroid artery arises off the branches of the thyrocervical trunk off the subclavian artery and the superior thyroid artery arises off the external carotid artery. In a radial approach, the radial artery is accessed using standard methodology. The catheter with occluder(s) is then tracked through the radial artery, to the brachial artery, to the axillary artery, to the subclavian artery, and then to the inferior thyroid artery. In yet another arterial approach, the catheter is tracked through the radial artery to the brachial artery, to axillary artery, to the subclavian artery, to the brachiocephalic trunk, to the carotid artery, and then to the superior thyroid artery. In one venous approach, the catheter and occluder are tracked through the superior vena cava, to the brachiocephalic vein, to the inferior thyroid vein. In another venous approach, the catheter and occluder are tracked through the superior vena cava, to the brachiocephalic vein, to the internal jugular vein, and the superior thyroid vein. Regardless of the approach, once the occluder is positioned in a vessel in close fluid communication with the thyroid, at least one occluder is expanded prior to and/or substantially simultaneously with the infusion of the treatment agent to constrain the flow of the treatment agent, and generate elevated downstream pressure of the occluder that creates deep penetration of the vessels of the thyroid with the treatment agent.

By way of another example, the systems and methods can be used in the treatment of cancers of the head and neck, which can be approached from either arterial access or venous access. In arterial access, the head and neck can be approached from at least the femoral or radial arteries. In a femoral approach, the iliac artery is accessed using standard methodology. The catheter with occluder(s) is then tracked to the aorta, and then to the aortic arch. From there, brachiocephalic trunk can be accessed, and the catheter is advance to the common carotid, and then to the superior laryngeal artery. Alternatively, the iliac artery is accessed using standard methodology. Then the catheter is tracked to the aorta, and then to the artic arch. From there, the brachiocephalic trunk is accessed, and the catheter is advanced through the common carotid, and then external carotid. Then, the facial artery, the alveolar artery, or the maxillary artery can be selected depending on tumor location. In a radial approach, the radial artery is accessed using standard methodology. The catheter with occluder(s) is then tracked through the radial artery, to the brachial artery, to the axillary artery, to the subclavian artery, and then to the brachiocephalic trunk. Then, the catheter is advance to the common carotid and the external carotid. From there, the facial artery, the alveolar artery, or the maxillary artery can be selected depending on tumor location. In a radial approach, the radial artery is accessed using standard procedure, and then the catheter is tracked through the radial artery to the brachial artery, to axillary artery, to the subclavian artery, to the brachiocephalic trunk, to the common carotid, and then to the superior laryngeal artery. In one venous approach, the catheter and occluder are tracked through the superior vena cava, to the brachiocephalic vein, to the subclavian vein, to the external jugular vein, and to the anterior jugular vein. In another venous approach, the catheter and occluder are tracked through the superior vena cava, to the brachiocephalic vein, to the internal jugular vein, and the superior thyroid vein and to the laryngeal vein. In yet another venous approach, the catheter and occluder are tracked through the superior vena cava, to the brachiocephalic vein, to the internal jugular vein, and to the one of the facial vein, the alveolar vein, or the maxillary vein. Regardless of the approach, once the occluder is positioned in a vessel in close fluid communication with the target tissue of the head or neck requiring treatment, at least one occluder is expanded prior to and/or substantially simultaneously with the infusion of the treatment agent to constrain the flow of the treatment agent, and generate elevated downstream pressure of the occluder that creates deep penetration of the vessels of the target tissue with the treatment agent.

By way of another example, the systems and methods can be used in the treatment of cancers of the brain, which can be approached from an arterial access, a venous access, or a ventricular approach. In arterial access, the brain can be approached from at least the femoral or radial arteries. In a femoral approach, the iliac artery is accessed using standard methodology. The catheter with occluder(s) is then tracked to the aorta, and then to the aortic arch. From there, brachiocephalic trunk can be accessed, and the catheter is advance to the common carotid, and then to the internal carotid, and to the circle of willis. From there, the left and right middle cerebral artery or anterior cerebral arteries can be accessed. Alternatively, the brachiocephalic trunk can be accessed, and the catheter is advanced to the vertebral arteries, to the basilar artery, and to the circle of willis. From there, the left and right middle cerebral artery or anterior cerebral arteries can be accessed. In a radial approach, the radial artery is accessed using standard methodology. The catheter with occluder(s) is then tracked through the radial artery, to the brachial artery, to the axillary artery, to the subclavian artery, and then to the brachiocephalic trunk. Then, the catheter is advance to the common carotid, the internal carotid, and the circle of willis. From there, the left and right middle cerebral arteries, or the anterior cerebral arteries can be selected for access depending on tumor location. In an alternate radial approach, the catheter is advanced through the radial artery, to the brachial artery, to the axillary artery, to the subclavian artery, and then to the brachiocephalic trunk. Then, the catheter is advance to the vertebral arteries, to the basilar artery, and the circle of willis. From there, the left and right middle cerebral arteries, or the anterior cerebral arteries can be selected for access depending on tumor location. In one venous approach, the jugular vein is accessed using standard procedures and the catheter and occluder are advanced to the sigmoid sinus and then to the transverse sinus. From the transvers sinus, various access points can be reached. For example, the transvers sinus can be used to advance the catheter to the superior petrosal sinus, to the cavernous sinus, to the ophthalmic vein, to the sphenoparietal sinus, or to the posterior intercavernous sinus. Also, from the transvers sinus, access can be provided to the vein of Labbe and to the vein of Trolard. Also, from the transvers sinus, access can be provided to the straight sinus and to either the inferior sagittal sinus, the internal cerebral vein, or the basal vein of Rosenthal. Also, from the transverse sinus, access can be provided to the superior sagittal sinus and then to either the cortical vein or the vein of trolard. In a ventricular approach, a small incision is made in the scalp, and then a small hole is made in the skull. Once the hole is made in the skull, a small opening is made in the protective coverings of the brain. The incision, hole, and opening accommodate the catheter placement in the lateral ventricle. The device is then tracked to the target location in the interventricular foramen, third ventricle, aqueduct of midbrain, or fourth ventricle. Regardless of the approach, once the occluder is positioned in a vessel or ventricle in close fluid communication with the target tissue of the brain requiring treatment, at least one occluder is expanded prior to and/or substantially simultaneously with the infusion of the treatment agent to constrain the flow of the treatment agent, and generate elevated downstream pressure of the occluder that creates deep penetration of the vessels and/or ventricle of the target tissue with the treatment agent.

By way of another example, the systems and methods can be used in the treatment of cancers of the heart, which can be approached from either arterial access or venous access. In arterial access, the heart can be approached from at least the femoral or radial arteries. In a femoral approach, the iliac artery is accessed using standard methodology. The catheter with occluder(s) is then tracked to the aorta, and then to the aortic arch. From there, the catheter is advanced to the left main coronary artery to either the left anterior interventricular descending coronary artery or the left circumflex coronary artery. Alternatively, the iliac artery is accessed using standard methodology. Then the catheter is tracked to the aorta, and then to the aortic arch. From there, the catheter is advanced to the right main coronary artery to either the right posterior interventricular artery or the marginal artery. In a radial approach, the radial artery is accessed using standard procedure, and then the catheter is tracked through the radial artery to the brachial artery, to axillary artery, to the subclavian artery, to the brachiocephalic trunk, and then to the aortic arch. Then the catheter is advance to the left main coronary artery to either the left anterior interventricular descending coronary artery or the left circumflex coronary artery. Alternatively, the radial artery is accessed using a standard procedure. Then the catheter is advance through the radial artery to the brachial artery, to the axillary artery, to the subclavian artery, to the brachiocephalic trunk, and then to the aortic arch. Then, the catheter is advanced to the right main coronary artery and then to either the right posterior interventricular artery or the marginal artery. In a venous approach, the jugular vein is accessed using a standard procedure. Then the catheter is tracked through the brachiocephalic vein to the superior vena cava. Then the catheter is tracked to the coronary sinus and advanced to the great cardiac vein, the anterior cardiac vein, the middle cardiac vein, or the small cardiac vein. Regardless of the approach, once the occluder is positioned in a vessel in close fluid communication with the target tissue of the heart requiring treatment, at least one occluder is expanded prior to and/or substantially simultaneously with the infusion of the treatment agent to constrain the flow of the treatment agent, and generate elevated downstream pressure of the occluder that creates deep penetration of the vessels of the target tissue with the treatment agent.

By way of another example, the systems and methods can be used in the treatment of uterine and cervical cancers, which can be approached from arterial access from either the femoral or radial arteries. In a femoral approach, the iliac artery is accessed using standard methodology. The catheter with occluder(s) is then tracked to the interior iliac artery, then the vaginal artery, and then vaginal artery plexus. Alternatively, from the iliac artery, the device can be tracked to the interior iliac artery, then the uterine artery, and then uterine artery plexus. In a radial approach, the radial artery is accessed using standard procedure, and then the catheter is tracked through the radial artery to the brachial artery, to axillary artery, to the subclavian artery, to the brachiocephalic trunk, to the aortic arch, and then to the descending aorta. Then the device is further tracked to the iliac artery, further into the interior iliac artery, then the vaginal artery, and then vaginal artery plexus. Alternatively, from the subclavian artery, the catheter is tracked to through the aortic arch and then to the descending aorta. Then the tracking is continued through the iliac artery, to the interior iliac artery, then the uterine artery to the uterine artery plexus, to the aortic arch, and to the descending aorta. The tracking is further continued to the iliac artery, followed by the interior iliac artery, to uterine artery, and then to the uterine artery plexus. Regardless of the approach, once the occluder is positioned in a vessel in close fluid communication with the target tissue of the uterus or cervix, at least one occluder is expanded prior to and/or substantially simultaneously with the infusion of the treatment agent to constrain the flow of the treatment agent, and generate elevated downstream pressure of the occluder that creates deep penetration of the vessels of the target tissue with the treatment agent.

By way of another example, the systems and methods can be used in the treatment of ovarian tumors, which can be approached from arterial or venous access. Arterial access approaches can include either a femoral or radial artery approach, through the aorta to the ovarian artery branching off the aorta. Venous access can include tracking through the femoral vein to the external iliac vein, to the internal iliac vein, to the inferior vena cava to the ovarian veins. Regardless of the approach, once the occluder is positioned in a vessel in close fluid communication with the target tissue of the ovaries, at least one occluder is expanded prior to and/or substantially simultaneously with the infusion of the treatment agent to constrain the flow of the treatment agent, and generate elevated downstream pressure of the occluder that creates deep penetration of the vessels of the target tissue with the treatment agent.

By way of another example, the systems and methods can be used in the treatment of lung cancer, which can be approached from either arterial or venous access. In an arterial approach, the lungs can be accessed from either the femoral or radial arteries. From the femoral or radial arteries, the device is tracked to the aorta, and then to the bronchial artery off the aorta. In a venous approach, the lungs can be accessed from the femoral vein to the inferior vena cava, to the right atrium of the heart, to the right ventricle of the heart, and then into the pulmonary artery. Regardless of the approach, once the occluder is positioned in a vessel in close fluid communication with the target lung tissue, at least one occluder is expanded prior to and/or substantially simultaneously with the infusion of the treatment agent to constrain the flow of the treatment agent, and generate elevated downstream pressure of the occluder that creates deep penetration of the vessels of the target tissue with the treatment agent.

By way of another example, the systems and methods can be used in the treatment of kidneys, including renal cell carcinoma. The kidneys can be approached from either the arterial or venous sides. In an arterial approach, the kidneys can be accessed from either the femoral or radial arteries. From the femoral or radial arteries, the device is tracked to the aorta, and then to the renal artery off the aorta. In a venous approach, the lungs can be accessed from the femoral vein to the inferior vena cava, to the renal vein branching from the inferior vena cava. Regardless of the approach, once the occluder is positioned in a vessel in close fluid communication with the kidneys, at least one occluder is expanded prior to and/or substantially simultaneously with the infusion of the treatment agent to constrain the flow of the treatment agent, and generate elevated downstream pressure of the occluder that creates deep penetration of the vessels of the target tissue with the treatment agent.

Figure 23:
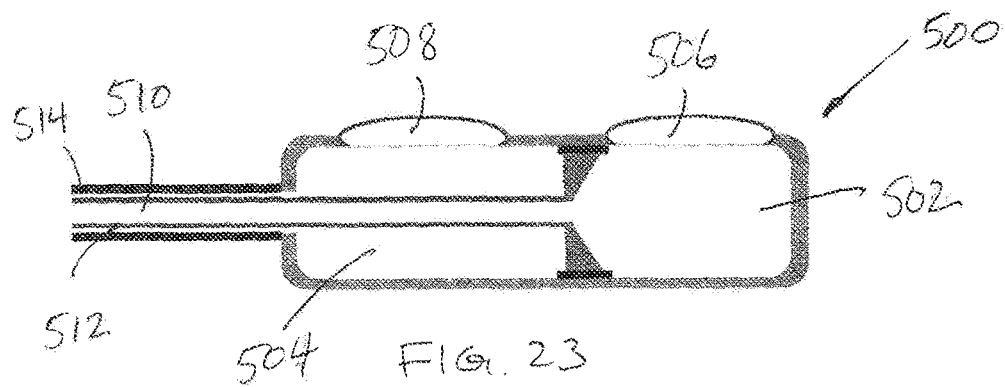
FIGS. 23 through 30B are schematic illustrations of various embodiments of implantable injection ports that can be used in association with the treatment system for performing pressure-controlled therapeutic delivery, in which figures identified with 'A' are shown in configurations in which an occluder would be collapsed, and figures identified with a 'B' are shown in configurations in which the occluder would be expanded for delivery of a therapeutic agent through the catheter.

In any of the foregoing embodiments and treatments, an injection port may be coupled at the proximal end of the catheter(s). While an injection port can be coupled for embodiments provided with two occlusion devices, it is anticipated that it may have greatest advantage with respect to long-term implantation of systems consisting of a single occlusion device, of which any of the foregoing systems can be so modified for use with the injection port. The injection port may be used externally of the patient, or may be implanted, preferably subdermally. By way of example, referring to FIG. 23, an injection port 500 includes a first chamber 502 and a second chamber 504, each having a respective needle pierceable septum 506, 508. The septa 506, 508 are adapted to be sufficiently self-healing such that fluid does not leak through the septa after they have been needle-pierced. The first chamber 502 is in fluid communication through the first lumen 510 of a first catheter 512 having a distal orifice. The second chamber 504, when filled, results in expansion of a static occluder coupled to the distal end of the second catheter 514. This may be effected in various ways.

In a first example, the static occluder is fluid inflatable, such as an elastic or inelastic balloon (e.g., balloon 328, as shown in FIG. 20), and the second chamber 504 is in fluid communication with an interior of the static occluder. Injection of an inflation fluid, e.g., saline, under pressure into the second chamber 504 causes the static occluder to expand sufficiently to extend across a vessel's walls and occlude the vessel thereat. Injection of a therapeutic agent or another fluid, e.g., saline, into the first chamber 502 under pressure causes the agent to exit the distal orifice, creates higher pressure than systemic pressure in the vessel distal of the expanded static occluder, and can optionally results in substantially simultaneous automatic expansion of a dynamic occluder (located distal of the first occluder) across the vessel's wall.

Figure 24A:
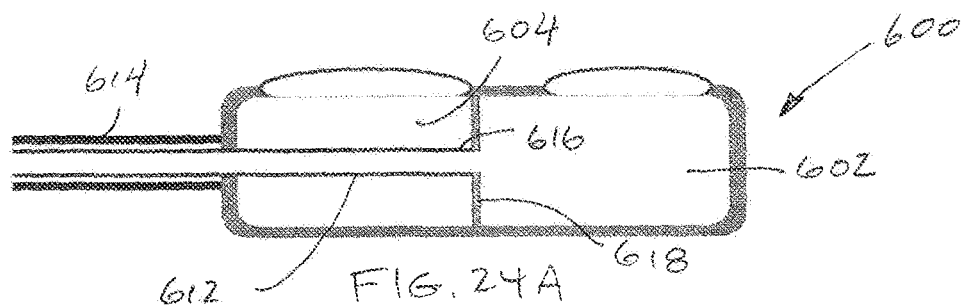
Figure 24B:
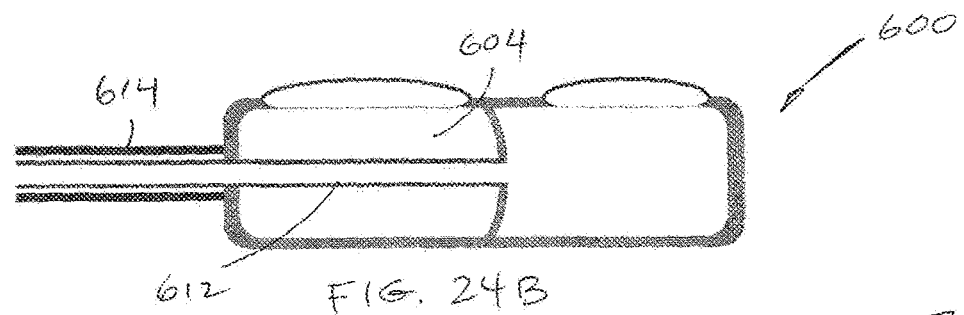

Referring to FIG. 24A, in a second example of an implantable port 600, the static occluder is a malecot-type device, in which the static occluder is expanded by relative longitudinal displacement of proximal and distal portions thereof. In the example shown, a first inner catheter 612 extends through and optionally beyond a second outer catheter 614. The static occluder is provided proximal of the distal end of the second outer catheter 614. The first chamber 602 is in fluid communication with the proximal end 616 of the first catheter 612. The second chamber 604 is closed; however, the second chamber 604 includes an elastically deformable wall 618 to which the proximal end 616 of the first catheter 612 is attached. As shown in FIG. 24B, injection of a fluid into the second chamber 604 causes the second chamber to deform into an expanded volume. As the second chamber expands, the first catheter 612 is drawn proximally relative to the second catheter 614 to expand the static occluder. Then, injection of a therapeutic agent or another fluid into the first chamber 602 under pressure causes the agent to exit the distal orifice, and creates higher pressure than systemic pressure in the vessel on the distal side of the expanded static occluder. By drawing fluid out of the second chamber 604 with a syringe or via a release valve, the deformed wall 618 is permitted to reform its shape, and the static occluder is thereby reduced in diameter or collapsed.

Figure 25A:
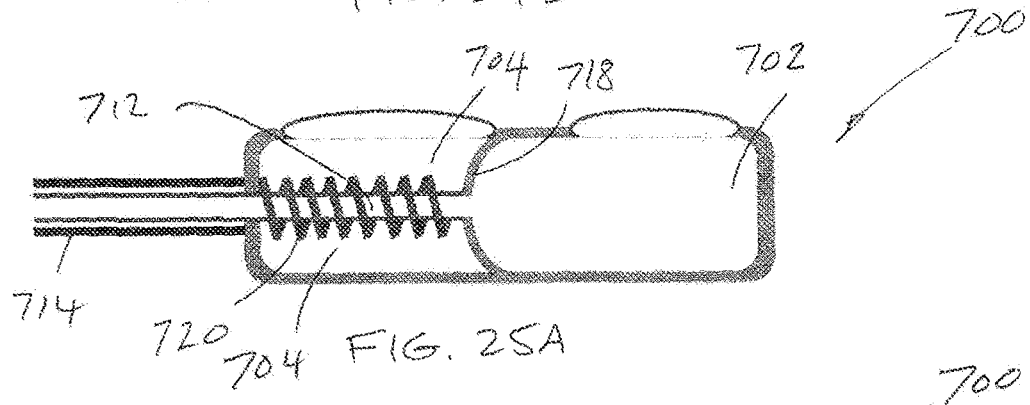
Figure 25B:
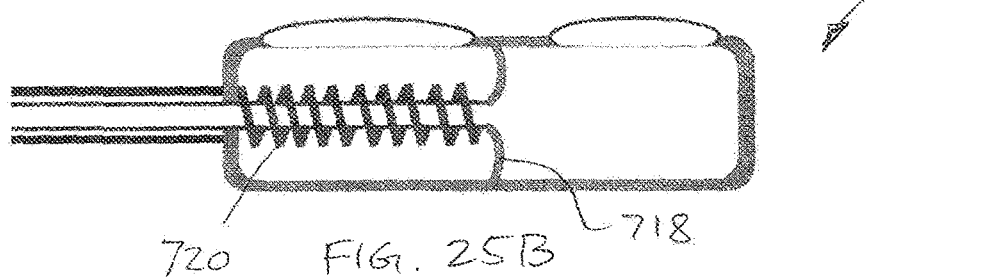

Turning to FIG. 25A, in a third example of an implantable port 700, substantially similar to the second example shown in FIG. 24A, a tension spring 720 is provided over the proximal end of the first catheter to deform a wall 718 and thereby bias the second chamber 704 toward a reduced volume and the first catheter 712 into a relatively distal position in which the static occluder is collapsed. As shown in FIG. 25B, injection of a fluid into the second chamber 704 causes the second chamber to deform against the bias of the spring 720 into an expanded volume. As the second chamber 704 expands, the first catheter 712 is drawn proximally relative to the second catheter 714 to expand the static occluder. Then, injection of a therapeutic agent or another fluid into the first chamber 702 under pressure causes the agent to exit the distal orifice, and create higher pressure than systemic pressure in the vessel on the distal side of the expanded static occluder. By drawing fluid out of the second chamber 704 with a syringe through the second septum 708 or via a release valve, the spring 720 is permitted to draw the wall 718 back to its prior shape, and the static occluder is thereby reduced in diameter or collapsed.

Figure 26A:
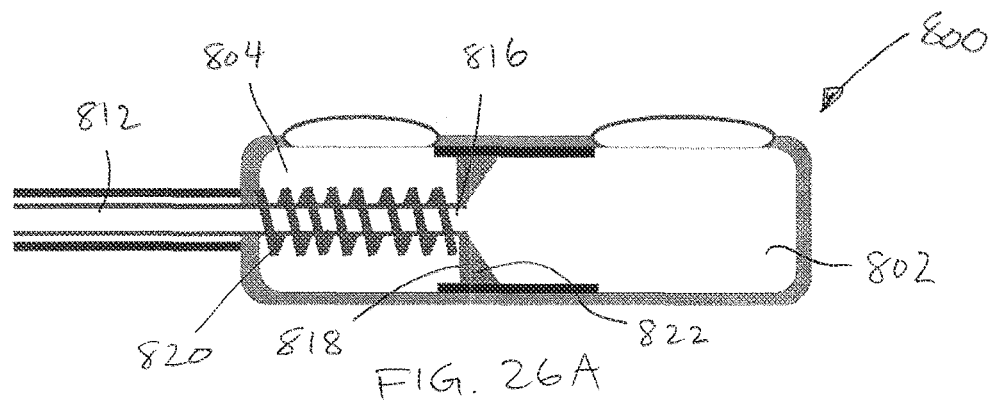
Figure 26B:
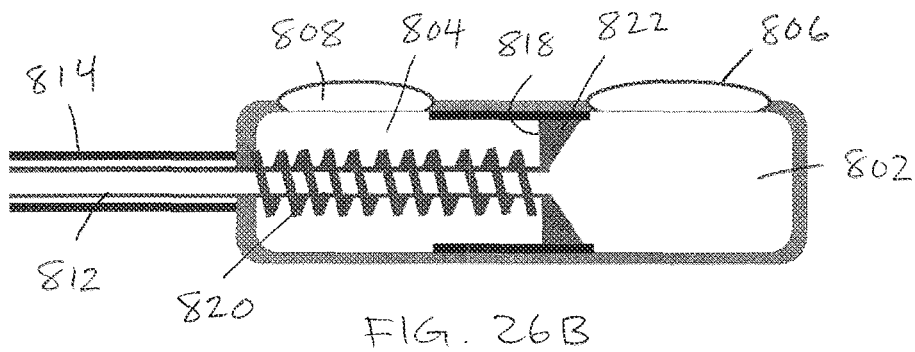

Referring to FIG. 26A, in a fourth example of an implantable port 800 substantially similar to the example shown in FIG. 25A, the static occluder is a malecot-type device, in which the static occluder is expanded by relative longitudinal displacement of proximal and distal portions thereof. The first chamber 802 is in fluid communication with the proximal end 816 of the first catheter 812. The second chamber 804 is closed off from the catheters, and includes a movable wall 818 as a part of a longitudinally-displaceable piston 822 to which the proximal end 816 of the first catheter 812 is attached. A tension spring 820 is provided to bias the piston 822 toward a reduced chamber volume. As shown in FIG. 26B, injection of a fluid through the second septum 808 into the second chamber 804 causes the wall 818 to displace on the piston 822 and expand the volume of the second chamber 804, against the bias of the spring 820. As the second chamber 804 expands, the first catheter 812 is drawn proximally relative to the second catheter 814 to expand the static occluder. Then, injection of a therapeutic agent or another fluid through the first septum 806 into the first chamber 802 under pressure causes the agent to exit the distal orifice at the end of the first catheter, and creates higher pressure than systemic pressure in the vessel on the distal side of the expanded static occluder. By drawing fluid out of the second chamber 804 with a syringe or via a release valve, the piston 822 is permitted to distally displace in accord with the bias of the spring 820, and the static occluder is thereby reduced in diameter or collapsed.

Figure 27A:
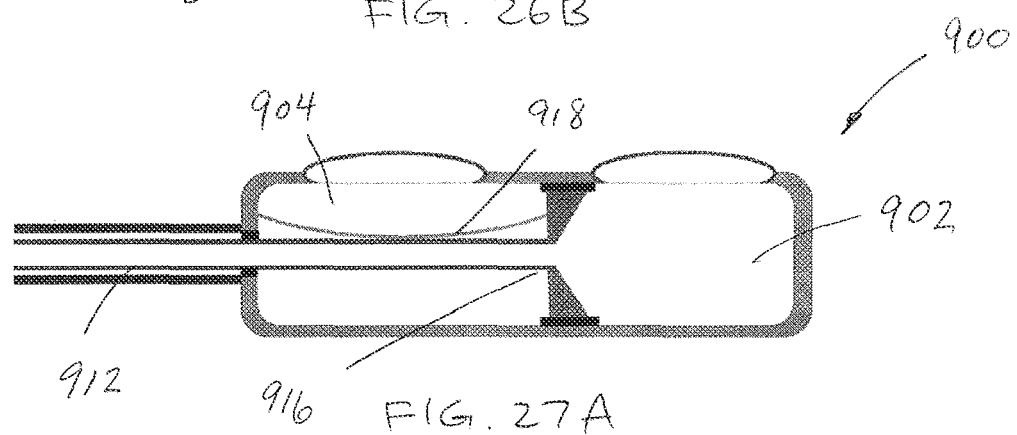
Figure 27B:
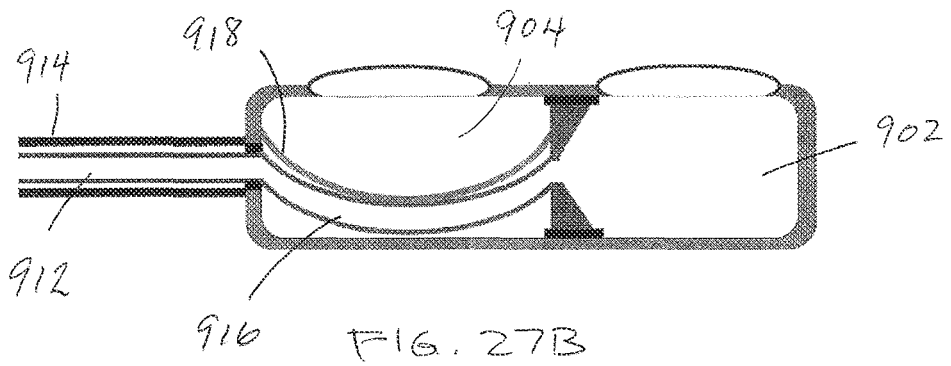

Referring to FIG. 27A, in a fifth example of an implantable injection port 900, the static occluder is a malecot-type device, in which the static occluder is expanded by relative longitudinal displacement of proximal and distal portions thereof. The first chamber 902 is in fluid communication with the proximal end 916 of the first catheter 912. The second chamber 904 is closed, and includes a deformable wall 918 extending outside but adjacent the proximal end 916 of the first catheter 912. The deformable wall 918 is located such that the axis of the first catheter does not intersect the deformable wall 918. As such, the second chamber 904 is separated from the first catheter 902. Turning to FIG. 27B, injection of a fluid into the second chamber 904 causes the deformable wall 918 to distend, and contact and displace the proximal end 916 of the first catheter 912. Such displacement causes the first catheter 912 to be proximally-displaced relative to the second catheter 914 and expand the static occluder. Then, injection of a therapeutic agent or another fluid into the first chamber 902 under pressure causes the agent to exit the distal orifice, and creates higher pressure than systemic pressure in the vessel on the distal side of the expanded static occluder. By drawing fluid out of the second chamber 904 with a syringe or via a release valve, the deformable wall 918 is released from displaceable contact with the first catheter 912, and the first catheter distally displaces relative to the second catheter 914 to permit the static occluder to collapsed in diameter.

Figure 28A:
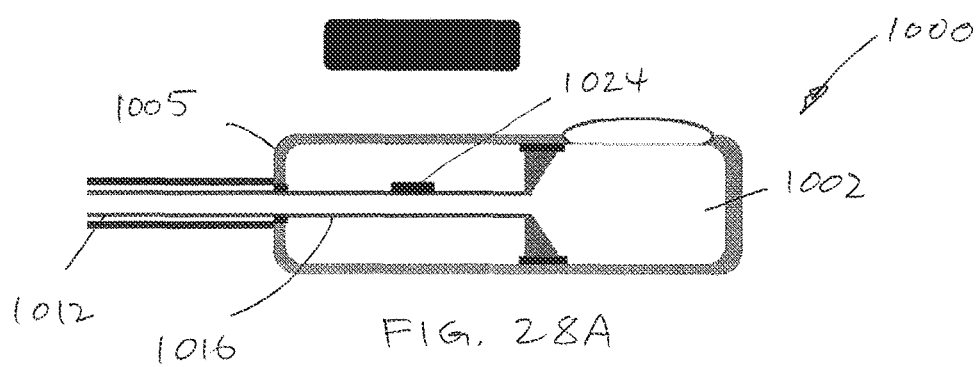
Figure 28B:
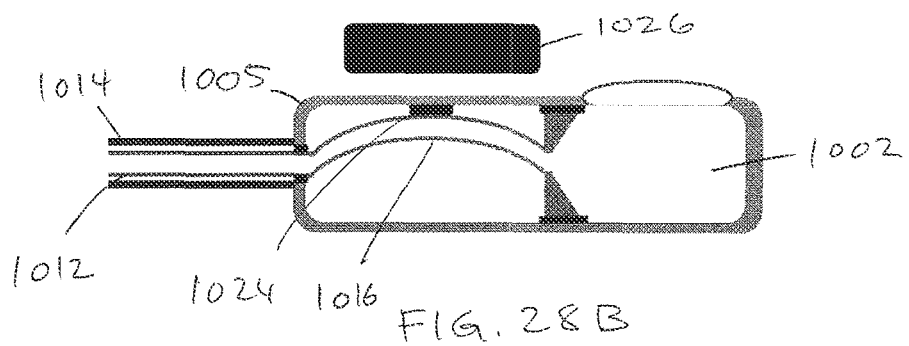

Referring to FIG. 28A, in a sixth example of an injection port 1000, the static occluder is a malecot-type device, in which the second occluder is expanded by relative longitudinal displacement of proximal and distal portions thereof. The injection port 1000 includes a single fluid chamber 1002, which is in fluid communication with the proximal end 1016 of the first catheter 1012. A second portion 1005 of the injection port is a housing through which the proximal end of the first catheter extends. The proximal portion 1016 of the first catheter 1012 is provided with first magnet 1024. Turning to FIG. 28B, when a second magnet 1026, external of the housing 1005 and having opposing facing polarity, is brought into magnetic association with the first magnet 1024, the first magnet 1024 is drawn toward the second magnet 1026. This causes the proximal portion 1016 of the first catheter 1012 to deform within the housing 1005 and results in longitudinal displacement of the first catheter 1012 relative to the second catheter 1014, which expands the static occluder. Then, injection of a therapeutic agent or another fluid into the first chamber 1002 under pressure causes the agent to exit the distal orifice of the first catheter, and creates higher pressure than systemic pressure in the vessel on the distal side of the expanded static occluder. The static occluder can be reduced in diameter by removing the second magnet 1026 from its magnetic association with the first magnet 1024, permitting the proximal portion 1016 of the first catheter 1012 to be released from its deformation.

Figure 29A:
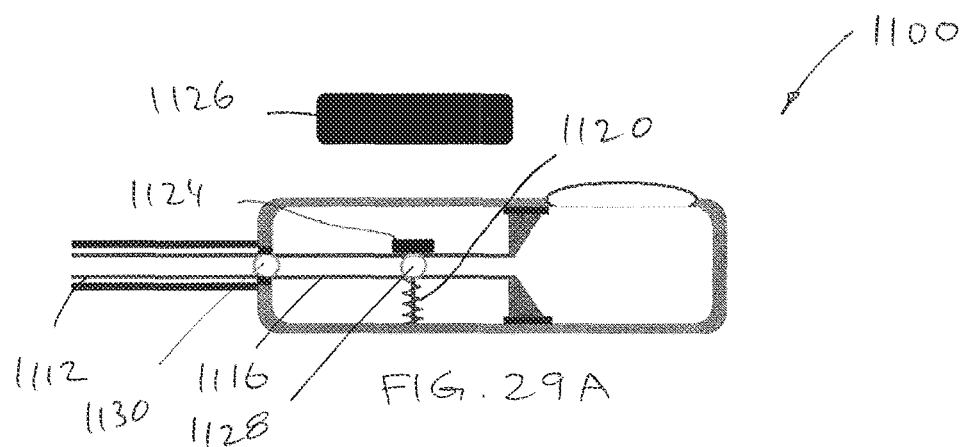
Figure 29B:
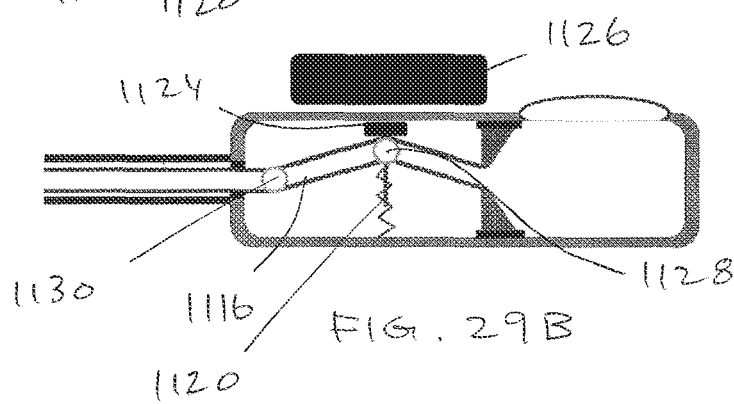

Referring to FIG. 29A, in a seventh example of an injection port 1100 substantially similar to the sixth example, the proximal portion 1116 of the first catheter 1112 may be formed with one or more pivot joints 1128, 1130. A spring 1120 may be coupled to the proximal portion 1116 of the first catheter opposite the first magnet 1124 to bias the proximal portion 1116 of the first catheter 1112 into a relatively straight configuration. Turning to FIG. 29B, when the second magnet 1126 is brought into magnetic association with the first magnet 1124, the first magnet 1124 is drawn toward the second magnet 1126, pulling the proximal portion 1116 of the first catheter against the bias of the spring 1120, and axially deforming the catheter at the pivot joint 1128. When the second magnet 1126 is removed, the spring 1120 assists in straightening the proximal portion 1116 to, in turn, collapse the static occluder.

Figure 30A:
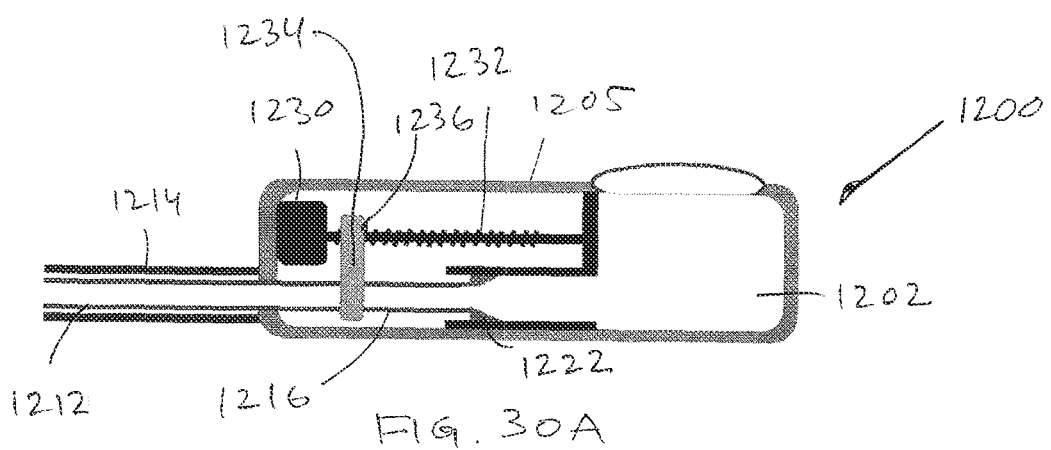
Figure 30B:
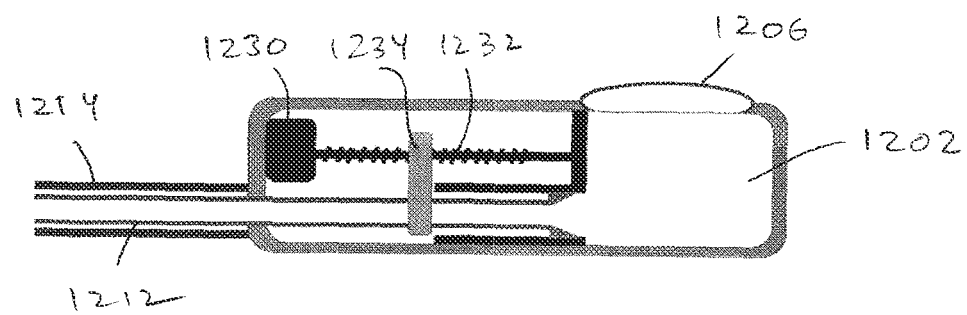

Referring to FIG. 30A, in an eighth example of an injection port 1200, the static occluder is a malecot-type device in which the static occluder is expanded by relative longitudinal displacement of proximal and distal portions thereof. The proximal portion 1216 of the first catheter 1212 is coupled to a piston 1222 that is longitudinally displaceable relative to the second catheter 1214. The first chamber 1202 is in fluid communication with the proximal end 1216 of the first catheter 1212. An electric motor 1230 is provided in the housing 1205. The motor 1230 rotates a threaded rod 1232. An arm 1234 having a threaded hole 1236 extends over the threaded rod 1232 and is fixed to the proximal portion 1216 of the first catheter 1212. Turning to FIG. 30B, when the motor 1230 is actuated, the threaded rod 1232 rotates causing longitudinal displacement of the arm 1234 and thus the first catheter 1212 relative to the second catheter 1214. The motor 1230 is activated to open the static occluder. Then, a therapeutic agent or another fluid is injected into the first chamber 1202 through the septum 1206 under pressure to cause the agent to exit the distal orifice of the first catheter 1212, to create higher pressure than systemic pressure in the vessel on the distal side of the expanded static occluder. The static occluder can be reduced in diameter by actuating the motor 1230 in reverse.

In each of the injection port embodiments, optionally a dynamic occluder can be provided distal of the static occluder and automatically expanded upon the increase in vessel pressure generated distal of the static occluder upon infusion of the therapeutic agent. Moreover, embodiments provided with the injection port at the proximal end of the first catheter can be used where localized intra-arterial infusion is desirable over an extended period of time in order to control the disease state. In such cases, an infusion pump or the described injection port or another injection port is used to administer therapy for extended periods of time. The occlusion device is advanced to the target vasculature, and the proximal injection port is implanted in the patient, preferably subdermally but easily accessible to a needled syringe. Then, at prescribed administration periods, the injection port can be used to deliver a bolus of fluid into the second chamber of the port to cause expansion of the static occlusion device, as well as deliver a separate bolus of medication into the first chamber of the port to deliver medication out the distal orifice. This is all done without requiring a physician to re-access the target vasculature. Further, the bolus of medication in the first chamber can be followed up with a bolus of saline under a relatively higher pressure to advance the flow of the therapeutic agent into the target vessels under a relatively higher pressure than that which it was originally infused; i.e., to provide reduced stress to the medication while passing through the catheter, yet provide reproducible cannulization into the target organs and tissues, and deep penetration of the medication into the target vessels.

There have been described and illustrated herein embodiments of treatment systems and methods for pressure-controlled therapeutic delivery. While particular embodiments of the invention have been described, it is not intended that the invention be limited thereto, as it is intended that the invention be as broad in scope as the art will allow and that the specification be read likewise. Thus, while particular embodiments include preferred dimensions for the occlusion elements in relation to particular vessels in around the pancreas, it will be appreciated that the system can be adapted for a treatment provided through vessels in and around other organs, and the occlusion elements can be likewise adapted for extending completely across the relevant vessels of such other organs. Also, while the system is primarily adapted for therapeutic treatment of humans, it has been demonstrated on porcine tissues and organs, and can be used for the treatment of mammals, in general. Both humans and animals shall be considered 'patients' for purpose of this application. Further, while the systems has been described for treatment via the portal vein, the system and the pressure-responsive methods of use, may also be used to infuse treatment agents during arterial side infusions. Moreover, while various exemplar therapeutics have been disclosed, the system and methods are not limited to any specific therapeutic agent. By way of further example, and not by limitation, checkpoint inhibitors and oncolytic virus can also be used as the therapeutic agent. Also, combinations of therapeutic agents may be infused. While particular dimensions and ratios have been disclosed, it will be understood that the invention is not limited thereto. Further, while specific catheters, occluders, etc. that have been referenced with respect to the terms 'first' and 'second' in relation to the devices disclosed herein, the terms 'first' and 'second' with respect to such elements does not indicate that one is primary or more important, or require that the first be provided in order to have the second. Moreover, the terms 'first' and 'second' can be used interchangeably with respect to such described components, as either catheter or occluder could have been designated as a 'first' or a 'second'. While various exemplar features of different embodiments are shown and described, it is fully within the teaching set forth herein that embodiments using various compatible and/or adaptable features described herein are within the explicit scope of the described inventions. It will therefore be appreciated by those skilled in the art that yet other modifications could be made to the provided invention without deviating from its scope as claimed.

What is claimed is:

1. A method for delivering a therapeutic agent for treatment of a solid tumor in a target organ, the target organ in fluid communication with a vein in a patient, the method comprising:
   a) introducing a treatment system into the vein of the patient, the treatment system comprising a microvalve comprising a filamentary braid coated with a polymeric filter comprising pores, the microvalve movable between a collapsed configuration for delivery through the vein, and an expanded configuration adapted to extend across the vein;
   b) advancing the microvalve into the vein in the collapsed configuration, the vein subject to a systemic venous pressure on a distal side of the microvalve; then
   c) expanding the microvalve into the expanded configuration to block flow within the vein in a distal to proximal direction past the microvalve; and
   d) injecting the therapeutic agent at a first pressure, distal of the microvalve and into the vein to cause the therapeutic agent to flow through the vein and into the target organ at a pressure higher than the systemic venous pressure, wherein a pressure of the injected therapeutic agent generates a net increase in fluid pressure in the vein of 10 mmHg to 200 mmHg above the systemic venous pressure.

2. The method according to claim 1, wherein:
the first pressure is below 300 psi.

3. The method according to claim 1, wherein:
the microvalve is dynamic such that the microvalve automatically expands to the expanded configuration and contracts to a smaller configuration in response to fluid pressure within the vein on proximal and distal sides of the microvalve, wherein in the smaller configuration the microvalve is not adapted to block flow within the vein.

4. The method according to claim 3, wherein:
the microvalve is located on a catheter, the catheter comprising a proximal end, a distal end, a first lumen extending between the proximal and distal ends and having a distal orifice, and the microvalve located at the distal end, proximal of the distal orifice.

5. The method according to claim 1, wherein:
the treatment system further comprises is a static occlusion element.

6. The method according to claim 5, wherein:
the static occlusion element is a balloon.

7. The method according to claim 4, wherein:
the proximal end of the catheter comprises an implantable injection port, and
further comprising implanting the implantable injection port in the patient and injecting a bolus of a second agent, such that the injecting the therapeutic agent and the injecting the bolus of the second agent both occur through the implanted injection port.

8. The method according to claim 1, wherein:
the therapeutic agent comprises one of a radio-embolization agent and a biologic agent.

9. The method according to claim 1, wherein:
the therapeutic agent is a biologic agent selected from the group consisting of one of CAR-T cells, CAR-NK cells, TCR-R cells, TCR-NK cells, B-cells, and a combination of two or more of the cells.

10. The method according to claim 1, wherein:
the therapeutic agent comprises one or more of a biologic cell, a checkpoint inhibitor, and an oncolytic virus.

11. The method according to claim 1, wherein:
the target organ is one of the pancreas, the kidneys, and the liver.

12. The method according to claim 1, wherein:
the vein is a portal vein or a feeder vessel extending therefrom.

13. The method according to claim 1, wherein:
the vein is a splenic vein or a feeder vessel extending therefrom.

14. A method for delivering a therapeutic agent under pressure to a target organ for treatment of a solid tumor in the target organ, the target organ in fluid communication with a vein in a patient, the method comprising:
a) introducing a treatment system into the vein of the patient, the treatment system comprising a microvalve comprising a filamentary braid coated with a polymeric filter comprising pores, the microvalve movable between a collapsed configuration for delivery through the vein, and an expanded configuration adapted to extend across the vein;
b) advancing the microvalve in the collapsed configuration into the vein, wherein the vein is subject to a systemic venous pressure on a distal side of the microvalve; then
c) expanding the microvalve into the expanded configuration across the vein to block flow within the vein in a distal to proximal direction past the microvalve; and
d) injecting the therapeutic agent at a first pressure below 300 psi to exit distal of the microvalve and into the vein to cause the therapeutic agent to flow through the vein at a pressure higher than the systemic venous pressure and into the target organ, the therapeutic agent comprising a biologic agent selected from the group consisting of one of CAR-T cells, CAR-NK cells, TCR-R cells, TCR-NK cells, B-cells, and a combination of two or more of the cells.

15. The method according to claim 14, wherein:
the target organ is one of the pancreas, the kidneys, and the liver.

16. The method according to claim 14, wherein:
the vein is a portal vein or a feeder vessel extending therefrom.

17. The method according to claim 14, wherein:
the vein is a splenic vein or a feeder vessel extending therefrom.

18. A method for delivering a therapeutic agent under pressure to a target organ for treatment of a solid tumor in the target organ, the target organ in fluid communication with a vein in a patient, the method comprising:
a) introducing a treatment system into the vein of the patient, the treatment system comprising a microvalve comprising a filamentary braid coated with a polymeric filter comprising pores, the microvalve movable between a collapsed configuration for delivery through the vein, and an expanded configuration adapted to extend across the vein;
b) advancing the microvalve in the collapsed configuration into the vein, wherein the vein is subject to a systemic venous pressure on a distal side of the microvalve; then
c) expanding the microvalve into the expanded configuration across the vein to block flow within the vein in a distal to proximal direction past the microvalve; and
d) injecting the therapeutic agent at a first pressure below 300 psi to exit distal of the microvalve and into the vein to cause the therapeutic agent to flow through the vein at a pressure higher than the systemic venous pressure and into the target organ, the therapeutic agent comprising one or more of a biologic cell, a checkpoint inhibitor, and an oncolytic virus.

19. The method according to claim 18, wherein:
the target organ is one of the pancreas, the kidneys, and the liver.

20. The method according to claim 18, wherein:
the vein is a portal vein or a feeder vessel extending from the portal vein.

21. The method according to claim 18, wherein:
the vein is a splenic vein or a feeder vessel extending from the splenic vein.

22. A method for delivering a therapeutic agent under pressure to a target organ for treatment of a solid tumor in the target organ, the target organ in fluid communication with one or more vessels in a patient, the method comprising:
a) introducing a treatment system into a vessel of the patient in fluid communication with the target organ, the treatment system comprising a microvalve comprising a filamentary braid coated with a polymeric filter comprising pores, the microvalve having shape memory to an expanded configuration adapted to extend across the vessel;

b) advancing the microvalve into the vessel, wherein the vessel is subject to a systemic venous pressure on a distal side of the microvalve; then
c) expanding the microvalve across the vessel to block flow within the vessel in a distal to proximal direction past the microvalve;
d) injecting the therapeutic agent at a first pressure below 300 psi to exit distal of the microvalve and into the vessel to cause the therapeutic agent to flow through the vessel at a pressure higher than the systemic venous pressure and into the target organ, the therapeutic agent comprising a biologic agent selected from the group consisting of one of CAR-T cells, CAR-NK cells, TCR-R cells, TCR-NK cells, β-cells, and a combination of two or more of the cells; and
e) injecting a bolus of a second fluid different than the therapeutic agent at a second pressure at or above 300 psi, the second fluid entering the vessel and forcing the therapeutic agent to flow deeper through the vessel to therapeutically treat the solid tumor in the target organ with the therapeutic agent.

23. The method of claim 22, wherein the target organ is not located within an extremity.

24. A method for delivering a therapeutic agent under pressure to a target organ for treatment of a solid tumor in the target organ, the target organ in fluid communication with one or more vessels in a patient, the method comprising:

a) introducing a treatment system into a vessel of the patient in fluid communication with the target organ, the treatment system comprising a microvalve comprising a filamentary braid coated with a polymeric filter comprising pores, the microvalve having shape memory to an expanded configuration adapted to extend across the vessel;
b) advancing the microvalve into the vessel, wherein the vessel is subject to a systemic venous pressure on a distal side of the microvalve; then
c) expanding the microvalve across the vessel to block flow within the vessel in a distal to proximal direction past the microvalve;
d) injecting the therapeutic agent at a first pressure below 300 psi to exit distal of the microvalve and into the vessel to cause the therapeutic agent to flow through the vessel at a pressure higher than the systemic venous pressure and into the target organ, the therapeutic agent comprising one or more of a biologic cell, a checkpoint inhibitor, and an oncolytic virus; and
e) injecting a bolus of a second fluid different than the therapeutic agent at a second pressure at or above 300 psi, the second fluid entering the vessel and forcing the therapeutic agent to flow deeper through the vessel to therapeutically treat the solid tumor in the target organ with the therapeutic agent.

25. The method of claim 24, wherein the target organ is not located within an extremity.

* * * * *